(12) United States Patent
Yamada et al.

(10) Patent No.: US 7,560,484 B2
(45) Date of Patent: Jul. 14, 2009

(54) VACCINE PREPARATION CONTAINING FATTY ACID AS A CONSTITUENT

(75) Inventors: Haruki Yamada, Tokyo (JP); Hiroaki Kiyohara, Tokyo (JP); Takayuki Nagai, Tokyo (JP); Toshiaki Sunazuka, Chiba (JP)

(73) Assignee: The Kitasato Institute, Tokyo (JP)

( * ) Notice: Subject to any disclaimer, the term of this patent is extended or adjusted under 35 U.S.C. 154(b) by 779 days.

(21) Appl. No.: 10/363,484

(22) PCT Filed: Aug. 28, 2001

(86) PCT No.: PCT/JP01/07379

§ 371 (c)(1),
(2), (4) Date: Aug. 12, 2003

(87) PCT Pub. No.: WO02/17961

PCT Pub. Date: Mar. 7, 2002

(65) Prior Publication Data

US 2004/0024058 A1  Feb. 5, 2004

(30) Foreign Application Priority Data

Aug. 31, 2000  (JP) ............................. 2000-268390

(51) Int. Cl.
*A01N 37/00* (2006.01)
*A61K 31/21* (2006.01)
(52) U.S. Cl. .................. 514/513; 514/560; 514/627
(58) Field of Classification Search .................. 514/513, 514/560, 627
See application file for complete search history.

(56) References Cited

FOREIGN PATENT DOCUMENTS

EP  1 195 162 A1  4/2002

(Continued)

OTHER PUBLICATIONS

Yamada et al., Meth. Find. Exp. Clin. Pharmacol. vol. 20, No. 3, pp. 185-192, 1998.*

(Continued)

*Primary Examiner*—Deborah D Carr
(74) *Attorney, Agent, or Firm*—Townsend and Townsend and Crew LLP

(57) ABSTRACT

The present invention provides an adjuvant that is a hydroxy unsaturated fatty acid or a derivative thereof, as well as a vaccine preparation containing the adjuvant as a constituent. For example, a vaccine shows sufficient activity to enhance the immunity when a hydroxy unsaturated fatty acid having the following structure is administered:

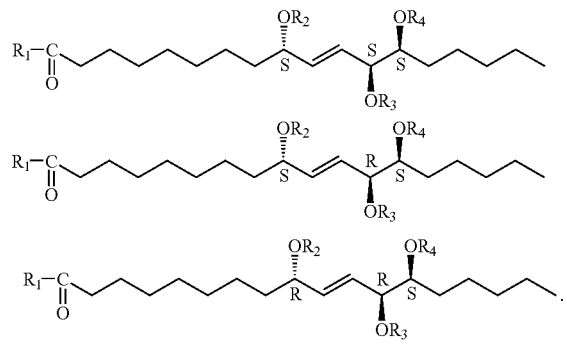

9 Claims, 4 Drawing Sheets

FOREIGN PATENT DOCUMENTS

| | | | |
|---|---|---|---|
| JP | 05-9130 | * | 1/1993 |
| JP | 5-009130 A | | 1/1993 |
| JP | 7-173069 A | | 7/1995 |
| WO | WO 96/06627 A1 | | 3/1996 |
| WO | 96/32964 | * | 10/1996 |
| WO | WO 96/32964 A1 | | 10/1996 |
| WO | WO 00/15257 A1 | | 3/2000 |
| WO | WO 00/23107 A1 | | 4/2000 |
| WO | WO 00/51634 A1 | | 9/2000 |

OTHER PUBLICATIONS

Maruno, Journal of Traditional Medicines, 1997, vol. 14, pp. 81-88.*

Yamada et al., Meth. Find. Exp. Clin. Pharmacol. vol. 20, No. 3, pp. 185-192, 1998.*

Nagai et al. Immunopharmacology and Immunotoxicology 20(2), 267-281, 1998.*

Kato, T. et al., "Structure and Synthesis of Unsaturated Trihydroxy $C_{18}$ Fatty Acids in Rice Plant Suffering From Rice Blast Disease," *Tetrahedron Letters*, 1985, pp. 2357-2360, vol. 26(19), Pergamon Press Ltd, Great Britain.

Nagai, T. et al., "In Vivo Anti-Influenza Virus Activity of Kampo (Japanese Herbal) Medicine "Sho-Seiryo-To"—Stimulation of Mucosal Immune System and Effect on Allergic Pulmonary Inflammation Model Mice," *Immunopharmacology and Immunotoxicology*, 1998, pp. 267-281, vol. 20(2), Marcel Dekker, Inc.

Nagai, T. et al., "Pinellic Acid From the Tuber of *Pinnellia Ternata* Breitenbach as an Effective Oral Adjuvant for Nasal Influenza Vaccine," *International Immunopharmacology*, 2002, pp. 1183-1193, vol. 2(8), Elsevier Science B.V.

Shirahata, T., et al., "Total Synthesis and Adjuvant Activity of All Stereoisomers of Pinellic Acid," *Bioorganic & Medicinal Chemistry Letters*, 2003, pp. 937-941, vol. 13(5), Elsevier Science Ltd.

Sunazuka, T., et al., "Total Synthesis of Pinellic Acid, a Potent Oral Adjuvant for Nasal Influenza Vaccine. Determination of the Relative and Absolute Configuration," *Tetrahedron Letters*, 2002, pp. 1265-1268, vol. 43, Elsevier Science Ltd.

Schröder, Ulf and Stefan B. Swenson; "Nasal and parenteral immunizations with diphtheria toxoid using monoglyceride/fatty acid lipid suspensions as adjuvants"; *Vaccine*; 1996; pp. 2096-2103; vol. 17; Elsevier Science Ltd.

Kelley, D., et al., "Effects of Dietary Arachidonic Acid on Human Immune Response", *Lipids* (1997) vol. 32, No. 4, pp. 449-456.

Maruno, M., "Research for Active Principles of Pinelliae Tuber and New Preparation of Crude Drug", *Journal of Traditional Medicines*, (1997), vol. 14, pp. 81-88.

Nagai, T., "In Vivo Anti-Influenza Virus Activity of Kampo (Japanese Herbal) Medicine "Sho-Seiryu-to"—Effects on Aged Mice, Against Subtypes of A Viruses and B Virus, and Therapeutic Effect", *Immunopharmacology and Immunotoxicology*, (1996) vol. 18, No. 2, pp. 193-208.

Parmentier, H., et al., "Dietary Unsaturated Fatty Acids Affect Antibody Responses and Growth of Chickens Divergently Selected for Humoral Responses to Sheep Red Blood Cells", *Poultry Science* (1997) vol. 76, pp. 1164-1171.

Yamada, H., et al., "In Vivo Antiinfluenza Virus Activity of Kampo Medicine Sho-Seiryu-To Through Mucosal Immune System", *Meth Find Exp. Clin. Pharmacol* (1998) vol. 20, No. 3, pp. 185-192.

Hamberg, M., et al., "Peroxygenase-Catalyzed Fatty Acid Epoxidation in Cereal Seeds," *Plant Physiol.*, vol. 110, pp. 807-815 (1996).

Lederer, M., et al., "Reactivity of Lysine Moieties toward an Epoxyhydroxylinoleic Acid Derivative: Aminolysis versus Hydrolysis," *J. Agric. Food Chem.*, vol. 47, pp. 4611-4620 (1999).

Masui, H., et al., "An Antifungal Compound 9, 12, 13-Trihydroxy-(E)-10-Octadecenoic Acid, From *Colocasia Antiquorum* Inoculated with *Ceratocystis Fimbriata*," *Phytochemistry*, vol. 28, No. 10, pp. 2613-2615 (1989).

Miyaichi, Y., et al., "Studies on the Constituents and Anatomical Characteristics of the Sparganii Rhizome Derived from *Sparganium stoloniferum* BUCH.-HAM.," *Natural Medicines*, vol. 49(1), pp. 24-28 (1995).

Quinton, P., et al., "Synthesis of Unsaturated Trihydroxy $C_{18}$ Fatty Acids," *Tetrahedron Letters*, vol. 32(37), pp. 4909-4912 (1991).

Merck Index, 12th Edition, p. 1413, No. 8378.

* cited by examiner

FIG. 2

VACCINE PREPARATION CONTAINING FATTY ACID AS A CONSTITUENT

TECHNICAL FIELD

The present invention relates to an adjuvant that contains a hydroxy unsaturated fatty acid as an active ingredient and to vaccine preparations containing the adjuvant as a constituent, such vaccine preparations being useful to prevent or treat diseases of human, animals, and other organisms.

BACKGROUND ART

Vaccines have been used to prevent various diseases, and have provided tremendous and excellent results in the prevention of specific diseases such as smallpox. Nonetheless, vaccines also have side effects and there are many cases in which vaccines are less effective. Thus there is much room for improvement in the field of vaccines. Currently, many types of vaccines used for human or other animals are prepared by using pathogenic organisms, or parts thereof, as antigenic materials for vaccine production. This means that there is no denying the possibility that vaccines are contaminated with constituents of pathogenic organisms or ingredients of growth medium for pathogenic organisms. These contaminants can cause adverse side effects upon vaccination. In addition, antigenic sites associated with immunization themselves can induce side effects when inoculated in large quantity.

Attempts have been made to avoid such side effects as much as possible and to manufacture safe vaccines. Such attempts include the reduction of inoculum dose of vaccine, the use of high-purity preparations of antigen for vaccine, and the alteration of vaccination routes. However, these revisions have a general problem—the immunological activity of such revised vaccines tends to be reduced. Accordingly, adjuvants have been used to prevent such a decline of immunological activity. In such cases, there remain some problems to be solved, such as improvement in effectiveness and safety of adjuvants.

For example, a pathogenic microorganism such as influenza virus infects via mucous membranes. To prevent such diseases at early stages of infection, vaccines capable of significantly enhancing local immunity on the mucous membrane rather than systemic immunity in the blood are preferred. In this context, it is also preferable to have an adjuvant capable of contributing to the enhancement of local immunity. At the same time, instead of injection, oral, transdermal, or intranasal inoculation is noteworthy as a vaccination route. The injection must be performed by medical technicians and is, therefore, problematic when it is necessary to vaccinate many people under a condition with no or only poor medical facilities. In contrast, oral, transdermal, and intranasal inoculation can be performed without direct practices by medically skilled staffs, so long as vaccine preparations are available. In general, when vaccinated with an injectable vaccine, via alternate vaccination route, sufficient immunological stimulation is difficult to attain and, therefore, certain adjuvants suitable for alternate vaccination routes are needed.

In other words, an important challenge for the development of vaccines is to develop an excellent adjuvant that is effective and safe and that helps the enhancement of required immunity at the desired site.

Previously, aluminum compounds (aluminum sulfate, aluminum hydroxide, etc.) and phosphate compounds (calcium phosphate, aluminum phosphate, etc.) have widely been used as adjuvants for vaccination. Currently, the gel of these compounds is almost the only adjuvant that is used for human vaccination. However, there are some problems in regard to these adjuvants, and thus the adjuvants are in need of improvement. Some illustrations are as follows:

1) Problems associated with manufacturing and handling: For example, since the quality of these adjuvants tends to vary from one production lot to another, they are not suited to large-scale manufacturing. Moreover, the handling is also inconvenient. For example, they are unsuitable for column operation. 2) A problem associated with their effect: While they excel in inducing the humoral immunity, they are not effective for inducing the cellular immunity, and thus there are limitations on the types of antigens to be used.

Studies and development of new types of adjuvants, such as saponin, are proceeding in order to overcome the drawbacks. Some illustrations are as follows (See J. C. Cox et al., Vaccine 15, 248-256, 1997):
1. Surface active substances, such as saponins.
2. Bacterial toxins, such as cholera toxin.
3. Constituents of microorganisms or plants, such as BCG, and muramyl peptide.
4. Cytokines, such as interleukins.
5. Synthetic polyanion, polycation.
6. Micro-carriers.

The present inventors have found that certain extracts of Chinese and Japanese traditional (Kampo) medicine, consisting of several crude drugs, exhibit adjuvant activity and increase the antibody titer against influenza virus in the nasal irrigation liquid and in the serum when used as an ingredient of influenza vaccine to be inoculated intranasally (H. Yamada and T. Nagai, Methods and Findings in Experimental and Clinical Pharmacology, 20(3), 185-192, 1998). However, exactly which component(s) of the extract has the adjuvant activity remains to be clarified.

DISCLOSURE OF THE INVENTION

An objective of the present invention is to provide a novel method for enhancing the immunological activity of vaccine in order to produce vaccines whose immunological activity is not reduced when dosage is lowered or vaccination route is altered. More specifically, the objective is to screen for an effective and safe compound having a simpler structure among crude drug and to thereby develop a novel adjuvant. Chinese and Japanese traditional (Kampo) medicines have long been used clinically in China, Japan, and other Asian countries, and its effectiveness and safety have been already established. Thus, the medicines are excellent and suitable as the material to be utilized for the present objective.

In other words, an objective of the present invention is to provide a hydroxy unsaturated fatty acid and derivatives thereof as novel, effective, and safe vaccine adjuvants, to provide vaccines composed of these, and to contribute to the manufacture of effective and safe vaccines.

In a preferred embodiment, the present invention provides an adjuvant that contains 9S,12S,13S-trihydroxy-10E-octadecenoic acid, 9S,12R,13S-trihydroxy-10E-octadecenoic acid, or 9R,12R,13S-trihydroxy-10E-octadecenoic acid, or a derivative thereof.

The inventors have previously revealed that a hot-water extract from a Chinese and Japanese traditional medicine "Sho-seiryu-to (Xiao-Qing-Long-Tang in Chinese)", which consists of 8 kinds of medicinal plants, has an adjuvant activity, and that the extract elevates the antibody titer against influenza virus in the nasal irrigation liquid as well as in the serum when orally administered in combination with intranasal inoculation of influenza vaccine (H. Yamada and T. Nagai, Methods and Findings in Experimental and Clinical Pharmacology, 20 (3), 185-192, 1998).

Thus, for the purpose of achievement of the above-mentioned objective, the inventors used hot-water extracts from the respective 8-kind medicinal plants, which are components of Sho-seiryu-to, as adjuvants to orally administer them in order to determine which component(s) exhibits the adjuvant activity to influenza vaccine upon nasal vaccination. The result showed that the hot-water extract from a medicinal plant "Pinelliae Tuber" had the highest adjuvant activity. Further, the present inventors separated and purified an active ingredient from the hot-water extract of Pinelliae Tuber and analyzed its structure, and found a fatty acid (9S,12S,13S-trihydroxy-10E-octadecenoic acid) having a particular structure exhibited strong activity of enhancing immunity. In addition, the present inventors synthesized a homologous fatty acid having a different absolute structure from that of 9S,12S,13S-trihydroxy-10E-octadecenoic acid derived from Pinelliae Tuber, and found 9S,12R,13S-trihydroxy-10E-octadecenoic acid and 9R,12R,13S-trihydroxy-10E-octadecenoic acid which have the strong immunopotentiating activity like 9S,12S,13S-trihydroxy-10E-octadecenoic acid, thereby completing the present invention. Specifically, a means for solving the above-mentioned objective can be established by the following inventive adjuvant and a vaccine preparation using this adjuvant:

(1) an adjuvant comprising a hydroxy unsaturated fatty acid or a derivative thereof;

(2) the adjuvant of (1), wherein the hydroxy unsaturated fatty acid or the derivative thereof is an unsaturated fatty acid with 18 carbon atoms that has a trihydroxy-monoene structure or a derivative thereof;

(3) the adjuvant of (2), wherein the unsaturated fatty acid with 18 carbon atoms that has a trihydroxy-monoene structure or the derivative thereof is 9,12,13-trihydroxy-10E-octadecenoic acid or a derivative thereof represented by the formula:

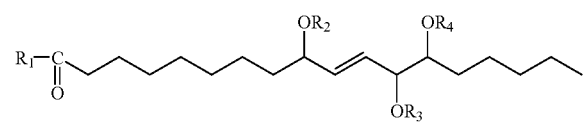

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group;

(4) the adjuvant of (3), wherein 9,12,13-trihydroxy-10E-octadecenoic acid or a derivative thereof is represented by any one of the formulae (I) to (III);

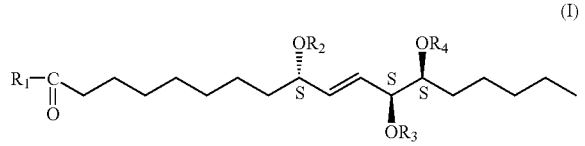

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group;

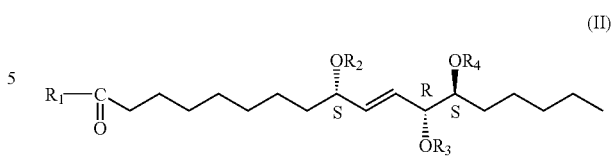

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group;

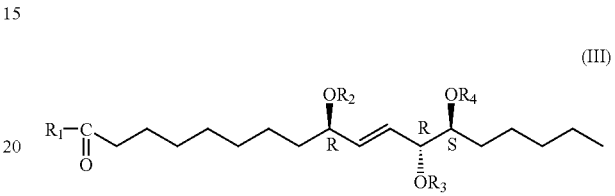

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group;

(5) a vaccine preparation comprising the adjuvant of any one of (1) to (4) as a constituent;

(6) the vaccine preparation of (5), wherein the adjuvant in the vaccine preparation is orally or transdermally administered independently of an antigen constituent;

(7) the vaccine preparation of (5) or (6), wherein an antigen constituent in the vaccine preparation is inoculated intranasally, subcutaneously, orally, transdermally, intramuscularly, or through mucosa by the other route;

(8) the vaccine preparation of any one of (5) to (7), wherein the vaccine preparation comprises, as an antigen constituent, one or more antigens from pathogenic microorganisms selected from the group consisting of influenza virus, rotavirus, measles virus, rubella virus, mumps virus, AIDS virus, *Bordetella pertussis*, diphtheria bacillus, *Helicobacter pylori*, enterohaemorrhagic *Escherichia coli* (EHEC), *Chlamydia, Mycoplasma,* Malaria *Plasmodium*, coccidium, and schistosome;

(9) a method for administering the vaccine preparation of any one of (5) to (8), wherein the method comprises orally or transdermally administering the adjuvant in the vaccine preparation independently of the antigen constituent; and

(10) a method for administering the vaccine preparation of any one of (5) to (8), wherein the antigen constituent is inoculated intranasally, subcutaneously, orally, transdermally, or intramuscularly, or through mucosa by the other route.

The term "adjuvant" in the present invention refers to a substance capable of stimulating the immune system and thereby enhancing the immune response to an antigen.

Also, such a phrase "vaccine preparation comprising an adjuvant as a constituent" in the present invention encompasses not only the embodiment wherein the adjuvant is mixed with other constituents that can be components of a vaccine preparation, such as immunogenic constituents, but also the embodiment wherein the adjuvant is separated from other constituents that can be components of a vaccine preparation, such as immunogenic constituents. For example, even when an antigen constituent and an adjuvant are prepared separately and administered into a living body through an independent route, the two together are referred to as a vaccine preparation.

The adjuvant of the present invention is characterized by being a hydroxy unsaturated fatty acid or derivative thereof. The hydroxy unsaturated fatty acid to be used as an adjuvant belongs to a class of compounds comprising 18 carbons and preferably having three hydroxyl groups and a double bond (more particularly, having a trihydroxy-monoene structure). Such a compound is novel as a fatty acid adjuvant, in terms of containing hydroxyl groups and a double bond on the chain of fatty acid thereof. The hydroxyl groups and the double bond on the chain of fatty acid can be positioned on any carbons except those of the carboxylic acid. Also, when each hydroxyl group is separately linked to a different carbon, the hydroxyl group can be in a R- or S-configuration, and both configurations are allowable in the present invention. Further, the existence of two modes of linkage between the double bond and the substituent results in two configurations represented by E and Z; in this case, both configurations are also allowable.

In the context of maintaining or improving adjuvant activity, preferable positions of the hydroxyl groups and the double bond are exemplified as follows: hydroxyl groups are preferably at the positions of 9, 12, and 13; and position and configuration of the double bond are preferably 10 and E, respectively. Such compounds includes, for example, 9,12,13-trihydroxy-10E-octadecenoic acid.

A particularly desirable position of a hydroxy group and its configuration are such that a hydroxyl group has its position and an absolute configuration of 9S,12S,13S,9S,12R,13S, or 9R,12R,13S, and a double bond has its position and configuration of 10E. Among these fatty acids, 9S,12S 13S-trihydroxy-10E-octadecenoic acid is described as 10-octadecenoic acid, 9,12,13-trihydroxy-[9S-(9R*,10E,12R*, 13R*)], 9S,12R,13S-trihydroxy-10E-octadecenoic acid as 10-octadecenoic acid, 9,12,13-trihydroxy-[9S-(9R*,10E, 12S*,13R*)], 9R,12R,13S-trihydroxy-10E-octadecenoic acid as 10-octadecenoic acid, 9,12,13-trihydroxy-[9R-(9R*, 11E,12R*,13S*)] in the CAS nomenclature.

In the published literature, 9S,12S,13S-trihydroxy-10E-octadecenoic acid is described as phytoalexins of rice, and purification from a vegetable crude drug of Umbelliferae has been reported, but the adjuvant activity in a vaccine has not been reported (M. Kobayashi, T. Tawara, T. Tsuchida and H. Mitsuhashi, Chemical and Pharmaceutical Bulletin, 38, 3169-3171, 1990; T. Kato, Y. Yamaguchi, N. Abe, T. Uyehara, T. Namai, M. Kodama and Y. Shiobara, Tetrahedron Letters, 26, 2357-2360, 1985). In addition, 9S,12R,13S-trihydroxy-10E-octadecenoic acid and 9R,12R,13S-trihydroxy-10E-octadecenoic acid have been found in beer, and its production by synthesis has been reported, but no physiological activities of these fatty acids have been reported (M. Hamberg, Chemistry and Physics of Lipids, 43, 55-67, 1987; M. Hamberg, Journal of Agricultural and Food Chemistry, 39, 1568-1572, 1991).

The adjuvant of the present invention includes derivatives in which various substituents are linked to the hydroxyl groups of the above-mentioned fatty acid and the carbonyl group of the carboxylate moiety thereof. Such derivatives include, for example, ester derivatives, in which an acyl group, such as acetyl group, benzoyl group, pyruvate group, or succinate group, is linked to the hydroxyl group; as well as ether derivatives, in which an alkyl group, such as ethyl group or methyl group, is linked to it. Further examples of substituents linked to the carbonyl group of carboxylate include: alkyloxy groups, such as hydroxyl group, ethyloxy group; aryloxy groups, such as benzyloxy group; thioalkyl groups, such as thioethyl group, or thioaryl group, amino group, primary amine, or secondary amine, etc.

Specifically such compounds include, for example,

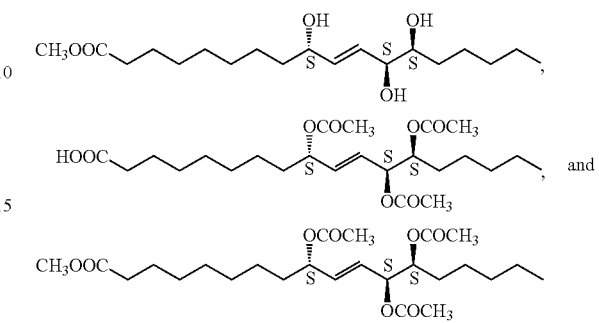

There are no reports on the strong adjuvant activity of a hydroxy unsaturated fatty acid having a trihydroxy-monoene structure including 9S,12S,13S-trihydroxy-10E-octadecenoic acid, 9S,12R,13S-trihydroxy-10E-octadecenoic acid, 9R,12R,13S-trihydroxy-10E-octadecenoic acid, and derivatives thereof in previously published literatures. The finding is novel and was first revealed by the present inventors based on their studies for long years. As described below, it is impossible to predict it, even based on descriptions in previous reports.

Known fatty acid compounds having adjuvant activity, of which structures have already been clarified, include linoleic acid and arachidonic acid (H. K. Parmentier, M. G. B. Nieuwland, M. W. Barwegen, R. P. Kwakkel and J. W. Schrama, Poultry Science, 76 (8), 1164-1171, 1997; D. S. Kelley, P. C. Taylor, G. J. Nelson, P. C. Schmidt, B. E. Mackey and D. Kyle, Lipids, 32 (4), 449-456, 1997). Although having 18 carbons, linoleic acid is different from the compound of the present invention in that it is a dienoic acid, which contains two double bonds; moreover, it is clearly distinct from the inventive compound in that it has no hydroxyl group. Arachidonic acid is a fatty acid having 20 carbons, four double bonds, and no hydroxyl group, and thus this compound is different from the inventive fatty acid.

So far it still remains to be clarified what mechanism underlies the strong adjuvant activity of the inventive hydroxy unsaturated fatty acid. However, the inventors have revealed that orally administered Chinese and Japanese traditional medicine "Sho-seiryu-to" exhibits the adjuvant activity of increasing the titer of anti-influenza virus IgA antibody in the nasal cavity when influenza vaccine is intranasally inoculated (T. Nagai, M. Urata and H. Yamada, Immunopharmacology and Immunotoxicology 18(2), 193-208, 1996). Further, the inventors have also found that oral administration of "Sho-seiryu-to" activates T lymphocytes in Peyer's patches, a tissue associated with induction of the mucosal immune system in the intestinal tract, as well as increases the number of cells producing influenza virus-specific IgA antibody among lymphocytes located in the nasal cavity (H. Yamada and T. Nagai, Methods and Findings in Experimental and Clinical Pharmacology 20 (3), 185-192, 1998; T. Nagai and H. Yamada, Immunopharmacology and Immunotoxicology 20(2), 267-281, 1998). There exists a common mucosal immune system in the mucosal immunity, and thus activation of any one of mucosal immune systems in the body results in the activation of other mucosal immune systems in other body areas, through distant immunity. Because 9S,12S,13S-trihydroxy-10E-octadecenoic acid among the adjuvants of the present invention has been identified as an essential substance exhibiting the adjuvant activity contained in Pinelliae Tuber that is medicinal plant constituting "Sho-seiryu-to," the fatty acid, like "Sho-seiryu-to", may activate the mucosal immune system in the intestinal tract to enhance the production of anti-influenza virus IgA antibody in the nasal cavity and thereby exhibiting the adjuvant activity.

1. Production of the Hydroxy Unsaturated Fatty Acid and Derivative Thereof

The fatty acids to be used in the present invention can be extracted, separated, purified, and manufactured from natural products, for example, animal tissues, medicinal plants, marine plants, and cultures of microorganisms used as a raw material, by the combined use of known methods. They can also be manufactured by chemical synthesis. Examples of the production methods are as follows:

A medicinal plant containing the fatty acid, Pinelliae Tuber (tuber of *Pinellia terhata* Breit except for the cork layer), is subjected to extraction with an organic solvent such as methanol or acetone, and the solvent is distilled off from the extract. The resulting residue is dissolved in water-containing methanol and extracted with a low polar solvent such as n-hexane or petroleum ether. The solvent is distilled off from the water-containing methanol layer. The resulting residue is fractionated, once or several times, by column chromatography using a carrier, for example, Sephadex such as Sephadex LH-20, a porous polymer such as DIAION HP-20, alumina, or silica gel and using at least one eluent selected from the group consisting of water, methanol, ethanol, chloroform, ether, n-hexane, benzene, and ethyl acetate. The constituent of interest is monitored by thin-layer chromatography. Thus, the fatty acid can be obtained. After the extraction of Pinelliae Tuber with water or the like, the fatty acid can be purified from the resulting water extract by ethanol precipitation, fractionation using a porous polymer such as DIAION HP-20, or a silica gel column chromatography. Alternatively, in some cases, it can be purified by recrystallization from an appropriate solvent such as acetone, methanol, and ethanol.

A known synthetic production by hydrolysis with epoxy alcohol has been reported (T. Kato, Y. Yamaguchi, N. Abe, T. Uyehara, T. Namai, M. Kodama, and Y. Shiobara, Tetrahedron Letters, 26, 2357-2360, 1985; M. Hamberg, Chemistry and Physics of Lipids, 43, 55-67, 1987).

Further, if desired, various derivatives can be prepared from the compound obtained as described above through methylation, ethylation, or benzoylation, by properly combining known chemical, biochemical, and genetic techniques.

The structure of the compounds of the present invention can be analyzed by known methods (W. Herz and P. Kulanthaivel, Phytochemistry, 24 (1), 89-91, 1985; S. Ohnuma, T. Uehara, T. Namai, M. Kodama, Y. Shiobara, Chemistry Letters, 577-580, 1986; M. Hamberg, Lipids, 26, 407-415, 1991; I. Ohtani, T. Kusumi, Y. Kashman, and H. Kakisawa, Journal of American Chemical Society, 113, 4092-4096, 1991; K. Kouda, T. Ooi, K. Kaya, and T. Kusumi, Tetrahedron Letters, 37, 6347-6350, 1996; M. Kobayashi, T. Tawara, T. Tsuchida, and H. Mitsuhashi, Chemical and Pharmaceutical Bulletin, 38, 3169-3171, 1990; K. Harada and K. Nakanishi, Accounts of Chemical Research, 5(8), 257-263, 1972).

2. Vaccine

New vaccine preparations, utilizing the inventive adjuvant, are also provided. The vaccine preparations of the present invention include vaccines in both narrow and broad senses. Specifically, the vaccines include:

i) vaccines in a narrow sense, which are effective against infectious diseases of human and other animals caused by virus, bacterium, fungus, protozoan, or other microorganisms. Examples of such vaccines include various vaccines such as influenza vaccine, *pertussis* vaccine, purified *pertussis*-diphtheria-tetanus combined vaccine, Japanese encephalitis vaccine, hepatitis A vaccine, hepatitis B vaccine, rotavirus vaccine, measles vaccine, rubella vaccine, mumps vaccine, measles-rubella-mumps combined vaccine, measles-rubella combined vaccine, and *Haemophilus influenzae* vaccine. The vaccines also include multi-drug resistant *Staphylococcus aureus* (MRSA) vaccine, *Helicobacter pylori* (abbreviated as *H. pyroli* hereafter) vaccine, enterohaemorrhagic *Escherichia coli* (EHEC) vaccine, *Salmonella* vaccine, *Chlamydia* vaccine, *Mycoplasma* vaccine, AIDS vaccine, malaria vaccine, coccidium vaccine, and schistosome vaccine.

ii) the vaccines in a broad sense are those effective for the prevention and treatment of non-infectious diseases, and include cancer vaccine, infertility vaccine, gastric ulcer vaccine, diabetic vaccine, and arteriosclerotic vaccine.

These vaccines include various vaccines that are categorized based on the types of methods for their production. Specifically, the vaccines include attenuated live vaccines, inactivated vaccines, component vaccines, and DNA-based vaccine. The DNA-based vaccines include vaccines containing a DNA fragment in a carrier such as plasmid, and vaccines used in combination with ribozymes or antisense oligonucleotides. These vaccines can be used for prevention and/or treatment. The vaccines also include recombinant vaccines containing, as their active ingredient, an antigen effective for vaccination, which is genetically produced in recombinant cells. These vaccines may be single vaccines or combined vaccines. Examples of their production methods and usage forms are described below.

Influenza vaccine—a split vaccine containing hemagglutinin (HA), neuramimidase (NA), nuclear protein (NP), matrix protein (M), or a part of these, which is obtained by proliferating the viruses in embryonated eggs or in Vero cells by using animal cell culture techniques, degrading the viruses with an agent such as ether and detergent, followed by purification, or by gene recombination techniques or chemical synthesis; or a DNA vaccine for intranasal inoculation comprising DNA fragments containing genes encoding these proteins.

*Pertussis* vaccine—an inactivated vaccine that is obtained by culturing *Bordetella pertussis*, treating the culture supernatant or bacteria by salting-out, ultracentrifugation to extract constituents of interest, and detoxicating the constituents with formalin; or a vaccine containing *pertussis* toxin (PT), filamentous hemagglutinin (FHA), 69 K membrane protein, or a partial peptide of these, derived from an artificial mutant strain that is prepared by gene recombination techniques or treatment with a mutagenizing agent.

*Pertussis*-diphtheria-tetanus combined vaccine—a triple vaccine prepared by mixing the above-described *pertussis* vaccine with diphtheria toxoid (DT) and tetanus toxoid (TT).

Japanese encephalitis vaccine—an inactivated vaccine that is obtained by proliferating the viruses in mouse brain or in Vero cells using animal cell culture techniques, purifying the virus particles by ultracentrifugation or with ethyl alcohol, and inactivating the virus with formalin; or a vaccine containing antigen proteins obtained by gene recombination techniques or chemical synthesis.

Hepatitis B vaccine—a plasma vaccine that is obtained by separating and purifying HBs antigen, by salting-out and ultracentrifugation, from blood collected from hepatitis B carriers as a raw material; or a recombinant vaccine containing the antigen portions obtained by gene recombination techniques or chemical synthesis.

Measles vaccine—a live vaccine of an attenuated virus that is prepared by proliferating the virus in culture cells such as chicken embryonic cells or in Vero cells using cell line culture techniques; a recombinant vaccine containing a part of the virus; or a recombinant vaccine containing a protective antigen prepared by gene recombination techniques or chemical synthesis.

Rubella vaccine—a vaccine containing the viruses grown in culture cells such as animal cells or human fetal cells or in Vero cells using cell line culture techniques; a part of the virus; or a protective antigen prepared by gene recombination techniques or chemical synthesis.

Mumps vaccine—an attenuated live vaccine containing the viruses grown in culture cells such as rabbit cells or in embryonated eggs; a part of the virus; or a protective antigen prepared by gene recombination techniques or chemical synthesis.

Measles-rubella combined vaccine—a dual vaccine that is obtained by mixing the above-described measles and rubella vaccines.

Measles-rubella-mumps combined vaccine—a triple vaccine that is obtained by mixing the above-described measles vaccine, rubella vaccine, and mumps vaccine.

Rotavirus vaccine—a vaccine containing the viruses grown in culture cells such as MA104 cell; the viruses collected from patient's feces; a part of the viruses; or a protective antigen prepared by gene recombination techniques or chemical synthesis.

AIDS vaccine—a vaccine containing the viruses grown in culture cells; the viruses obtained from patients; a part of these; a protective antigen prepared by gene recombination techniques or chemical synthesis; or a DNA vaccine containing effective DNA fragments.

*H. pylori* vaccine—a vaccine containing, as antigens, lysate of cultured *Helicobacter pylori*, or urease, heat shock protein, toxin, and others separated from cultured *Helicobacter pylori*; or a vaccine for injection, oral inoculation, or intranasal inoculation, which comprises these antigen proteins produced by gene recombination techniques.

3. Usage Forms of Adjuvant

There is no particular limitation on the usage forms for the adjuvants of the present invention as an active ingredient in a vaccine. In other words, the adjuvant can be used with various known appropriate usage patterns. For example, the adjuvant may be part of a physically mixed preparation or a complex chemically linked with an antigen protein. In addition, the adjuvant can be incorporated together with a vaccine in a carrier such as liposome.

The adjuvants of the invention can be used concurrently together with one or more conventional adjuvants. A preferable combination of the adjuvants of the present invention and conventional adjuvants can be empirically determined according to conditions to be considered, such as the type of antigens used as immunogens, the species of animals subjected to inoculation, and safety. The combination use can reduce adverse side reactions and enhance desired immunoreactivity, for example, by reducing the amount of antigen or the other adjuvant.

4. Method for Combining Adjuvant

The inventive vaccine preparation can be prepared by mixing the above-mentioned immunogen with the inventive adjuvant at an adequate mixing ratio. The inventive vaccine preparation can be effective even when the vaccine antigen (antigen constituent) and the inventive adjuvant are separately prepared as pharmaceutical preparations and then, as shown in the Examples, the two are separately inoculated, or the two are mixed with each other at the time of inoculation. The preparation must be done under strictly sterile conditions. Each of raw materials must be completely sterile. As a matter of course, to the extent possible, it is preferable that contaminants that are unnecessary for vaccination, including those that act as pyrogens or allergens, should be eliminated. Methods to achieve this objective are known to those skilled in the art.

5. Ratio of Adjuvant

The volume ratio between the vaccine antigen (antigen constituent) and the adjuvant in the vaccine preparation of the present invention can range, for example, from 1:0.0001 to 1:10,000 (weight ratio). The above range is merely a typical example. A suitable ratio is selected depending on the type of vaccine. Methods required for the selection are known to those skilled in the art.

6. Properties of Vaccine

The above vaccines are provided as liquid forms or powdered forms. If a powdered form is desired, the vaccines can be prepared as pharmaceutical preparations by a conventional method, including freeze-drying. Liquid forms of the pharmaceutical preparations are often suitable for the intranasal inoculation (intranasal spray, intranasal instillation, spread, etc.), oral administration, and injection. Alternatively, a powder spray can be provided for intranasal inoculation. The inventive vaccine preparation can also be formulated with publicly known stabilizers or preservatives. Such stabilizers include about 0.1 to 0.2% gelatin or dextran, 0.5 to 1% sodium glutamate, about 5% lactose, and about 2% sorbitol. Known preservatives include about 0.01% thimerosal, about 0.1% β-propionolactone, and about 0.5% 2-phenoxyethanol.

7. Method for Inoculating Vaccine Formulations

The vaccine preparation of the present invention can be utilized by any known method.

The inventive vaccine preparation can be used for inoculation as a mixture of a vaccine antigen (antigen constituent) and the adjuvant constituent. Alternatively, each constituent can be inoculated separately. The inoculation is preferably performed orally or intranasally. The effect of enhancing immunity can be achieved, even when the respective constituents are inoculated separately, for example, even when the vaccine antigen (antigen constituent) is intranasally inoculated and the adjuvant constituent is orally administered.

The dose to mouse is preferably 5 to 50 μl for intranasal inoculation or 0.05 to 0.5 ml for oral administration. The dose to human preferably ranges from about 0.1 to 1.0 ml for intranasal administration or about 1 to 100 ml for oral administration. The dose is changeable when desired. When combined with immunological antigen, for example, it has been believed that the following immunological antigens of pathogenic microorganism are advantageously inoculated intranasally, orally, or transdermally in terms of their vaccination effect or ease of inoculation:influenza virus, rotavirus, measles virus, rubella virus, mumps virus, human immunodeficiency virus, *Bordetella pertussis*, diphtheria bacillus, *H. pylori*, enterohaemorrhagic *Escherichia coli* (EHEC), *Chlamydia, Mycoplasma*, Malaria *Plasmodium*, coccidium, and schistosome.

These vaccine antigens (antigen constituent) and adjuvants can be inoculated singly or concurrently, for example, like *pertussis*-diphtheria-tetanus triple vaccine or measles-rubella dual vaccine. The intranasal and oral inoculations are preferable because mucous membranes of organs such as the respiratory tract and digestive tract can be infection routes. A suitable adjuvant with strong inducing activity of immune response is preferable in order to induce immune response in local mucous membranes that can be primary infection routes. Further, some vaccinations, such as vaccination against Malaria *Plasmodium*, are performed in most cases in regions without sufficient medical facilities. In such occasions, it is advantageous to select a vaccination route such as intranasal, oral, or transdermal inoculation route, thereby allowing a person who is not a technician such as physician or nurse, to perform the vaccination.

BRIEF DESCRIPTION OF THE DRAWINGS

FIG. 2 is a graph showing secondary production of antibodies in nasal irrigation liquids resulting from intranasal inoculation of an influenza vaccine used as the vaccine of the present invention. The ordinate indicates the antibody titer (ELISA unit) and the abscissa indicates the type of adjuvant used.

BEST MODE FOR CARRYING OUT THE INVENTION

Figure 1:
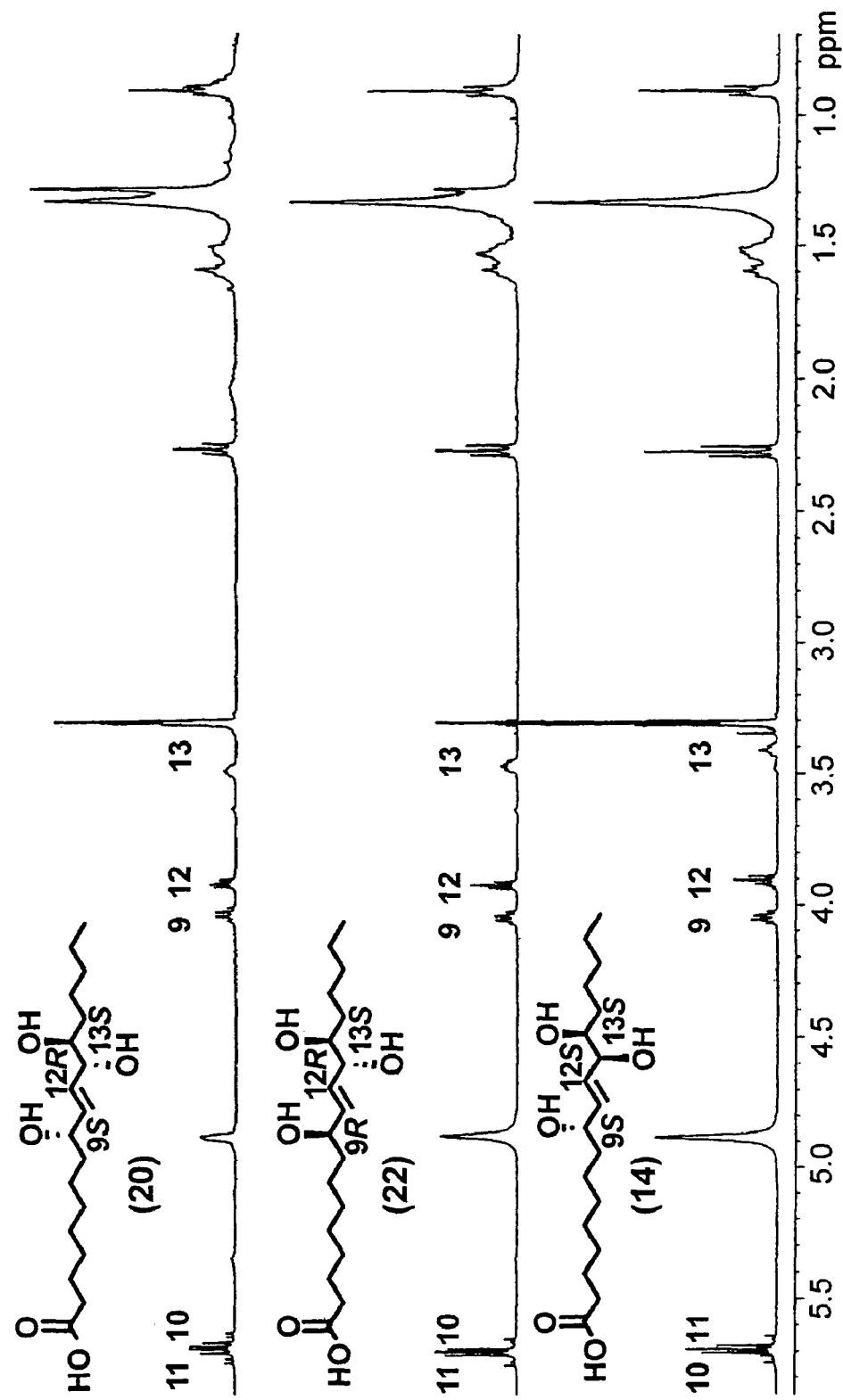
FIG. 1 shows proton nuclear magnetic resonance spectra of 9S,12S,13S-trihydroxy-10E-octadecenoic acid (14), 9S,12R,13S-trihydroxy-10E-octadecenoic acid (20), and 9R,12R,13S-trihydroxy-10E-octadecenoic acid (22), synthesized by the methods described in Examples 3 to 5, respectively. The ordinate indicates chemical shift (δ value, ppm) and the numeral indicates the number of assigned proton.

Herein below, the present invention will be specifically described with reference to Examples, but is not to be construed as being limited thereto.

Example 1

Preparation of 9S,12S,13S-trihydroxy-10E-octadecenoic Acid—(1)

9S,12S,13S-Trihydroxy-10E-octadecenoic acid was manufactured according to the method as described in Unexamined Published Japanese Patent Application (JP-A) No. Hei 3-258775 entitled "Fatty acid compound and antihypertensive agent comprising as an active ingredient the fatty acid compound.", the contents of which are herein incorporated by reference.

Pinelliae Tuber (1 kg) was extracted with methanol by heating, and the solvent was distilled off from the extract under reduced pressure to give 21.2 g of the methanol-extract. The methanol-extract was dissolved in 100 mL of a 90% (v/v) methanol-water mixed solution and transferred into a separatory funnel. After 50 mL of n-hexane was added, the funnel was shaken gently and then allowed to stand. The lower layer was recovered and concentrated up to half of the initial volume. The resulting concentrate was subjected to hydrophobic chromatography using a DIAION HP-20 (Mitsubishi Chemical) column. The elution was performed firstly with water, then with a 50% (v/v) methanol-water mixed solution, and finally with methanol. The methanol eluate fraction (530 mg) was subjected to column chromatography using Sephadex LH-20 (Amersham-Pharmacia Biotech), then to normal phase silica gel column chromatography, and finally to reverse phase high performance liquid chromatography using μ-Bondapak C18 (Millipore Waters) column to give 9S,12S,13S-trihydroxy-10E-octadecenoic acid as a colorless oily substance. The yield was 10 mg. The structure of this oily substance was determined by mass spectrum, nuclear magnetic resonance spectrum, specific rotation angle, and circular dichroismpolarization spectrum of an original compound and its derivative.

Rf=0.24 (silica gel plate, chloroform:methanol:acetic acid=10:1:0.1)

$[\alpha]_D^{28}$ −8.1° (c 0.32, methanol)

IR (KBr) ν $cm^{-1}$: 3430 (—OH), 1697 (—C=O), 1629 (—C=C—)

$^1$H-NMR (400 MHz, $CD_3OD$)

5.72 (1H, dd, J=15.9, 5.7 Hz, 10-H), 5.67 (1H, dd, J=15.9, 5.3 Hz, 11-H), 4.05 (1H, ddd, J=6.0, 5.7, 5.0 Hz, 9-H), 3.91 (1H, dd, J=5.7, 5.3 Hz, 12-H), 3.41 (1H, ddd, J=8.1, 5.7, 2.1 Hz, 13-H), 2.28 (2H, t, J=7.6 Hz, 2-$H_2$), 1.60 (2H, dt, J=7.6, 6.9 Hz, 3-$H_2$), 1.57-1.44 (2H, m, 8-$H_2$), 1.24-1.54 (16H, m, 4-, 5-, 6-, 7-, 14-, 15-, 16-, 17-$H_2$), 0.91 (3H, t, J=6.3 Hz, 18-$H_3$)

$^{13}$C-NMR (100 MHz, $CD_3OD$)

177.7 (C-1), 136.5 (C-11), 131.1 (C-10), 76.5 (C-12), 75.8 (C-13), 73.0 (C-9), 38.3 (C-8), 35.0 (C-2), 33.6 (C-14), 33.1 (C-16), 30.5*, 30.4* (*: C-4 or C-5), 30.2 (C-6), 26.6 (C-15), 26.4 (C-7), 26.1 (C-3) 23.7 (C-17), 14.4 (C-18)

High resolution mass spectrum (FAB, matrix: NBA)

found: m/z 353.2300 $[M+Na]^+$, calc.: m/z 353.2304 [M+Na] ($C_{18}H_{34}O_5Na$)

In addition, a derivative of 9S,12S,13S-trihydroxy-10E-octadecenoic acid was synthesized as follows and its structure was confirmed:

1) Synthesis of 12,13-O-isopropylidene-9,12,13-trihydroxy-10E-otcadecenoic Acid Methyl Ester Under the argon gas atmosphere, $TMSCHN_2$ (2.0 M in hexane, 29 mL, 58 mmol) was added dropwise to a benzene-methanol solution (10:1) (2.2 mL) of 9S,12S,13S-trihydroxy-10E-octadecenoic acid (9.6 mg, 29 μmol) at room temperature, and the mixture was stirred for 2.5 hours. Thereafter, the reaction solution was evaporated under reduced pressure, the resulting colorless oily crude product (10 mg) was dissolved in a dimethylformamide solution (0.6 mL) at room temperature under the argon gas atmosphere, and 2,2-dimethoxypropane (14 μL, 0.12 mmol) and PPTS (7.3 mg, 29 mmol) were added thereto, and the mixture was stirred at 60° C. for 48 hours. The temperature of the reaction solution was returned to room temperature, water (500 μL) was added to the reaction solution, and the mixture was extracted with chloroform (5 mL) three times. The organic layer was washed with saturated brine (3 mL), dried over anhydrous sodium sulfate, and concentrated. The resulting brown oily crude product (12 mg) was separated and purified by silica gel column chromatography (hexane:ethyl acetate=7:1) to obtain a colorless oily substance (12,13-O-isopropylidene-9,12,13-trihydroxy-10E-octadecenoic acid methyl ester) (11 mg, yield 100%).

2) Synthesis of 9-(4-bromobenzoyloxy)-12,13-O-isopropylidene-12,13-dihydroxy-10E-octadecenoic Acid Methyl Ester P-bromobenzoyl chloride (5.5 mg, 26 mmol) and DMAP (0.3 mg, 26 mmol) were added to a pyridine solution (500 μL) of the oily substance (1.0 mg, 2.6 mmol) obtained in 1) at room temperature under the argon gas atmosphere, and the mixture was stirred for 10 hours. Thereafter, water (0.5 mL) was added to the reaction solution, and the mixture was extracted with chloroform (3 mL) three times. The organic layer was washed with saturated brine (2 mL), dried over anhydrous sodium sulfate and concentrated. The resulting brown oily crude product (5 mg) was separated and purified by silica gel column chromatography (hexane:ethyl acetate=15:1) to obtain a colorless liquid substance (9-(4-bromobenzoyloxy)-12,13-O-isopropylidene-12,13-dihydroxy-10 E-otcadecenoic acid methyl ester) (1.0 mg, yield: 68%).

The physicochemical properties of this compound are as follows:

Rf=0.60 (silica gel plate, hexane:ethyl acetate=1:1)
$[\alpha]D^{22}10.0°$ (c 0.06, chloroform)
CD (c=5.3×10$^{-5}$, methanol) λmax (Δε): 244.8 (+6.97), 220.8 (+2.13) 209.1 (+5.97)
IR (KBr) ν cm$^{-1}$: 1724 (—C=O), 1633 (—C=C—)
$^1$H-NMR (400 MHz, CDCl$_3$)
7.89 (2H, d, J=8.9 Hz, 2-H, 6-H), 7.58 (2H, d, J=8.9 Hz, 3-H, 5-H), 5.84 (1H, dd, J=15.2, 7.0 Hz, 10-H), 5.76 (1H, dd, J=15.2, 6.8 Hz, 11-H), 5.50 (1H, dt, J=7.0, 6.0 Hz, 9-H), 3.99 (1H, dd, J=8.5, 6.8 Hz, 12-H), 3.67 (1H, m, 13-H), 3.66 (3H, s, —OCH$_3$), 2.29 (2H, t, J=7.9 Hz, 2-CH$_2$), 1.21-1.79 (20H, m, 3-, 4-, 5-, 6-, 7-, 8-, 14-, 15-, 16-, 17-CH$_2$), 1.41, 1.40 (3H each, s, C(CH$_3$)$_2$), 0.88 (3H, t, J=6.2 Hz, 18-CH$_3$)
$^{13}$C-NMR (100 MHz, CDCl$_3$)
137.9 (C-11), 131.7 (2C, Ar), 131.1 (2C, Ar), 130.7 (C-10), 81.6 (C-12) 80.8 (C-13), 74.7 (C-9), 51.4 (—OCH$_3$), 34.3 (C-8), 34.0 (C-2), 31.9 (C-14), 31.9 (C-16), 29.3 (C-6), 29.2*, 29.2* (*: C-4 and C-5), 27.3, 27.0 (—C(CH$_3$)$_2$), 25.6 (C-7), 25.0 (C-15), 24.9 (C-3), 22.5 (C-17) 14.0 (C-18)

High resolution mass spectrum (FAB, matrix: NBA)
found: m/z 589.2149 [M+Na]$^+$, calc.: m/z 589.2141 [M+Na] (C$_{29}$H$_{43}$O$_6$BrNa)

Example 2

Preparation of 9S,12S,13S-trihydroxy-10E-octadecenoic Acid—(2)

This Example describes the preparation of 9S,12S,13S-trihydroxy-10E-octadecenoic acid of the present invention from a hot-water extract of Pinelliae Tuber.

Pinelliae Tuber (500 g) was decocted with 10 L water until the volume of the solution was reduced to half of the initial one, and then the resulting extract was filtered. The residue was further decocted in the same manner. Both extracts were combined together and subjected to freeze-drying to yield a hot-water extract (yield: 19.8%). The hot-water extract was refluxed in 2.5 L of methanol to give methanol-soluble and methanol-insoluble fractions. The methanol-insoluble fraction was subjected to the same procedure two other times. After the methanol-insoluble fraction was again dissolved in water, four times as much volume as ethanol was added thereto and the resulting mixture was stirred overnight. The precipitate and supernatant were separated from each other. Further, the precipitate was dialyzed against distilled water by using a cellulose membrane with molecular-weight exclusion limit of 10,000, and then the inner dialysate was subjected to freeze-drying to give a non-dialyzable fraction (yield: 0.6%). The non-dialyzable fraction was dissolved in water and stirred together with DIAION HP-20. Then, the unabsorbed fraction was removed by washing the DIAION HP-20 with water. After the adsorbed substances were eluted by further washing with DIAION HP-20 with a 20% (v/v) and then with a 80% (v/v) methanol-water mixed solution, the adsorbed fraction was eluted with methanol to give a methanol-eluate fraction (yield: 0.06%). The methanol-eluate fraction was repeatedly purified by silica gel column chromatography to give the inventive 9S,12S,13S-trihydroxy-10E-octadecenoic acid. The yield was 0.35 mg.

In addition, the methanol-soluble fraction (45.4 g) obtained from a hot-water extract of Pinelliae Tuber by reflux in methanol was dissolved in 200 mL of a methanol-water mixed solution (9:1) then extracted with an equal volume of n-hexane while being shaken to obtain the lower layer. The solvent was distilled off from the lower layer under reduced pressure, and the resulting residue was stirred with DIAION HP-20 in an 80% methanol-water mixed solution. The unabsorbed fraction was removed by washing DIAION HP-20 with the same solvent. Further, the adsorbed fraction was obtained by eluting it from DIAION HP-20 with methanol. The adsorbed fraction was fractionated several times by silica gel column chromatography to give the inventive 9S,12S,13S-trihydroxy-10E-octadecenoic acid (1.2 mg).

Example 3

Synthesis of 9S,12S,13S-trihydroxy-10E-octadecenoic Acid (14)

Outline of a process for synthesizing 9S,12S,13S-trihydroxy-10E-octadecenoic acid is shown in schemes 1 and 2.

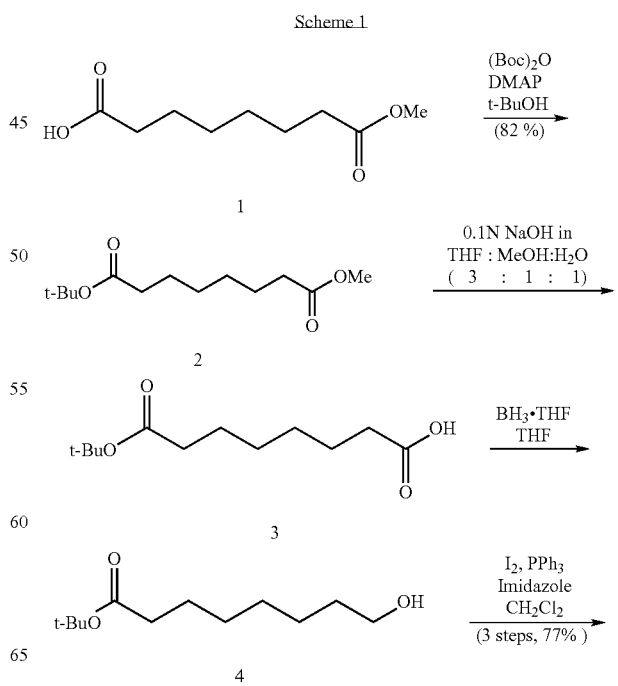

Scheme 1

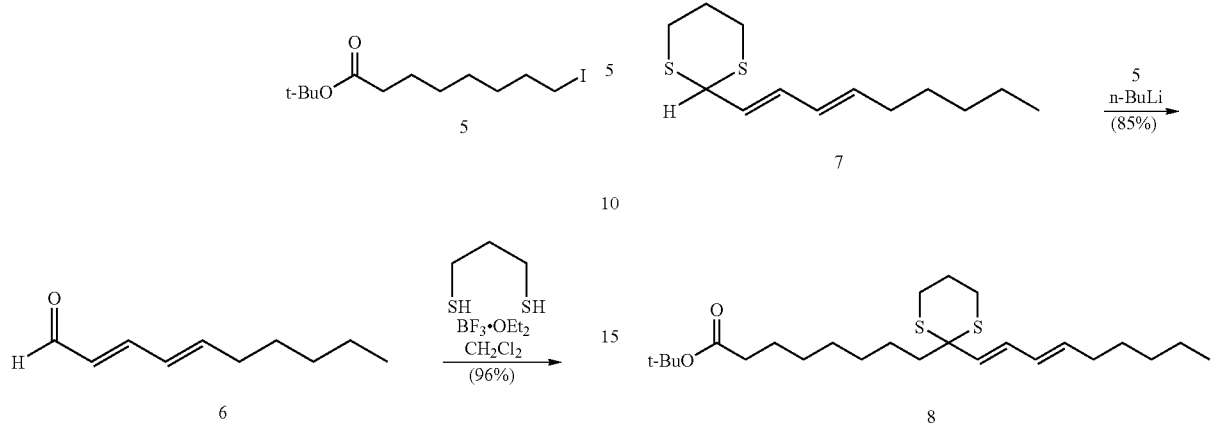
Scheme 2
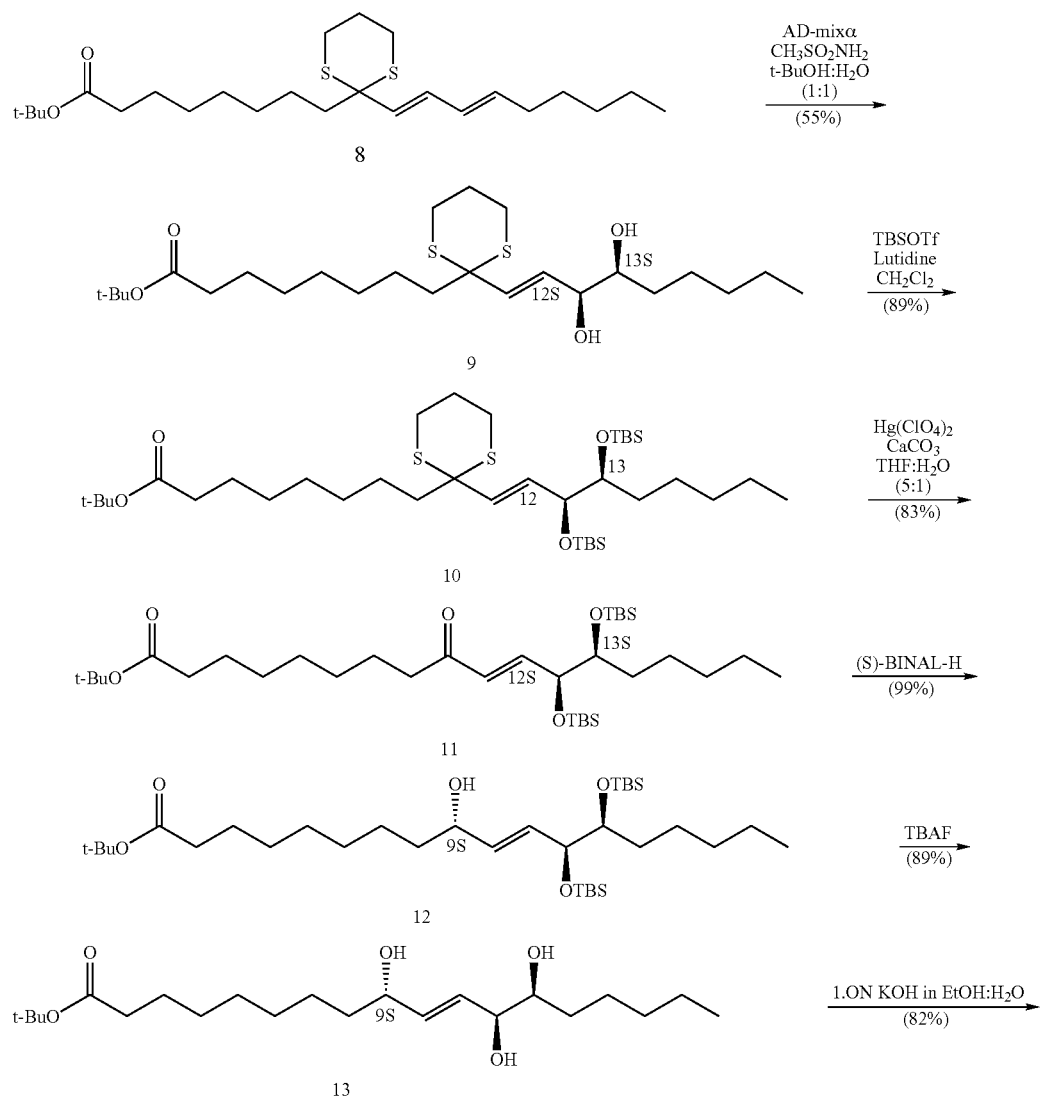

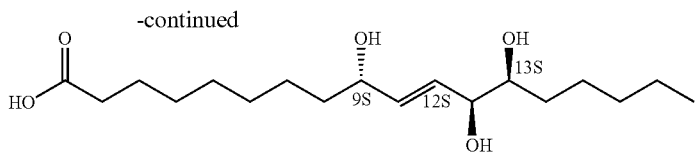

1) Synthesis of t-butyl-7-methoxycarbonylheptanoate (2)

Di-tert-butyl dicarboxylate (9.58 mL, 41.7 mmol) and 4-dimethylaminopyridine (1.02 g, 0.34 mmol) were successively added to a tert-butanol solution (56 mL) of 7-methoxycarbonylheptanoic acid (1) (5.00 mL, 5.24 g, 27.8 mmol) at room temperature under the argon atmosphere, and the mixture was stirred at room temperature for 1 hour. A 0.2 N hydrochloric acid solution (20 mL) was added to the reaction solution to make the mixture weakly acidic, and the reaction solution was concentrated to about ⅓ volume, and extracted with chloroform (50 mL) three times. The organic layer was washed with saturated brine (50 mL), dried over sodium sulfate, and concentrated. The resulting brown oily crude product (6.5 g) was separated and purified by silica gel column chromatography (hexane:ethyl acetate=10:1) to obtain t-butyl-7-methoxycarbonylheptanoate (2) as a colorless liquid substance (5.58 g, 82%).

Rf=0.41 (silica gel plate, hexane:ethyl acetate=5:1)
IR (KBr) ν cm$^{-1}$: 1734 (—C=O)
$^1$H-NMR (270 MHz, CDCl$_3$)
δ: 3.62 (3H, s, —OCH$_3$), 2.26 (2H, t, J=7.3 Hz, 7-H$_2$), 2.16 (2H, t, J=7.3 Hz, 2-H$_2$), 1.51-1.61 (4H, complex m, 3-, 6-H$_2$), 1.40 (9H, s, —C(CH$_3$)$_3$), 1.31-1.21 (4H, complex m, 4-, 5-H$_2$)
$^{13}$C-NMR (67.5 MHz, CDCl$_3$)
δ: 174.1 (C-8), 173.0 (C-1), 79.8 (—$\underline{C}$(CH$_3$)$_3$), 51.3 (—OCH$_3$), 35.4 (C-2) 33.9 (C-7), 28.7 (C-6), 28.6 (C-3), 28.0 (3C, —C($\underline{C}$H$_3$)$_3$), 24.8 (C-5) 24.7 (C-4)
High resolution mass spectrum (FAB, matrix: NBA)
found: m/z: 245.1750 [M+H]$^+$, calc.: 245.1753 [M+H] (C$_{13}$H$_{25}$O$_4$)

2) Synthesis of 7-t-butoxycarbonylheptanoic Acid (3)

t-Butyl-7-methoxycarbonylheptanoate (2) (5.51 g, 22.6 mmol) was added to a methanol-water-tetrahydrofuran (3:1:1) solution (113 mL) of 1.5 N sodium hydroxide at room temperature, and the mixture was stirred at room temperature for 28 hours. A 1.0 N hydrochloric acid solution (50 mL) was added to the reaction solution to make the mixture weakly acidic, the reaction solution was concentrated to about ⅓ volume, and extracted with chloroform (50 mL) three times. The organic layer was washed with saturated brine (50 mL), dried over sodium sulfate and concentrated. The resulting colorless liquid substance 7-t-butoxycarbonylheptanoic acid (3) (4.78 g, 92%) was used in the subsequent reaction without separation and purification.

Rf=0.52 (silica gel plate, chloroform:methanol=10:1)
IR (KBr) ν cm$^1$: 1732 (—C=O)
$^1$H-NMR (270 MHz, CDCl$_3$)
δ: 2.35 (2H, t, J=7.59 Hz, 7-H$_2$), 2.20 (2H, t, J=7.59 Hz, 2-H$_2$) 1.56-1.69 (4H, complex m, 3-, 6-H$_2$), 1.44 (9H, s, —C(CH$_3$)$_3$), 1.20-1.41 (4H, complex m, 4-, 5-H$_2$)

$^{13}$C-NMR (67.5 MHz, CDCl$_3$)
δ: 179.9 (C-8), 173.2 (C-1), 80.0 (—$\underline{C}$(CH$_3$)$_3$), 35.4 (C-2) 33.9 (C-7) 28.6 (C-6), 28.6 (C-3), 28.0 (3C, —C($\underline{C}$H$_3$)$_3$), 24.8 (C-5), 24.4 (C-4)
High resolution mass spectrum (FAB, matrix: NaI)
found: m/z: 253.1402 [M+Na], calc.: 253.1416 [M+Na] (C$_{12}$H$_{22}$O$_4$Na)

3) Synthesis of t-butyl-8-hydroxyoctanoate (4)

Boran tetrahydrofuran complex (1.0 M, 20.8 mL) was added dropwise to a tetrahydrofuran solution (41.6 mL) of 7-t-butoxycarbonylheptanoic acid (3) (4.78 g, 20.8 mmol) at 0° C. under the argon atmosphere. After the addition, the temperature of the reaction solution was raised to room temperature, and the solution was stirred at room temperature for 12 hours. Thereafter, saturated NaHCO$_3$ (50 mL) was added to the reaction solution, and the mixture was extracted with chloroform (50 mL) three times. The organic layer was washed with saturated brine (50 mL), dried over anhydrous sodium sulfate, and concentrated. The resulting colorless liquid substance t-butyl-8-hydroxyoctanoate (4) (4.45 g, 99%) was used in the subsequent reaction without separation and purification.

Rf=0.53 (silica gel plate, chloroform:methanol=10:1)
IR (KBr) ν cm$^{-1}$: 3430 (—OH), 1732 (—C=O)
$^1$H-NMR (270 MHz, CDCl$_3$)
δ: 3.26 (2H, t, J=6.6 Hz, 8-H$_2$), 1.81 (2H, t, J=7.6 Hz, 2-H$_2$), 1.12-1.22 (4H, complex m, 3-, 7-H$_2$), 1.05 (9H, s, —C(CH$_3$)$_3$), 0.88-0.99 (6H, complex m, 4-, 5-, 6-H$_2$)
$^{13}$C-NMR (67.5 MHz, CDCl$_3$)
δ: 173.3 (C-1), 79.9 (—$\underline{C}$(CH$_3$)$_3$), 62.7 (C-8), 35.5 (C-2) 32.5 (C-7) 29.0 (C-4), 28.9 (C-5), 28.0 (3C, —C($\underline{C}$H$_3$)$_3$), 25.5 (C-6) 24.9 (C-3)
High resolution mass spectrum (FAB, matrix: NaI)
found: m/z: 239.1630 [M+Na]$^+$, calc.: 239.1623 [M+Na] (C$_{12}$H$_{24}$O$_3$Na)

4) Synthesis of t-butyl-8-iodooctanoate (5)

Imidazole (2.10 g, 30.9 mmol), triphenylphosphine (8.10 g, 30.9 mmol), and iodine (6.27 g, 24.7 mmol) were successively added to a dichloromethane solution (100 mL) of t-butyl-8-hydroxyoctanoate (4) (4.45 g, 20.6 mmol) at 0° C. under the argon atmosphere, and the temperature of the reaction solution was raised to room temperature, followed by stirring for 2 hours. Thereafter, water (5 mL) was added to the reaction solution, and the mixture was washed successively with a 0.1 N aqueous sodium periodate solution (50 mL), 30% aqueous hydrogen peroxide (50 mL), and saturated brine (50 mL), dried over magnesium sulfate, and concentrated. The resulting brown oily crude product (21 g) was separated and purified by silica gel column chromatography (hexane:ethyl acetate 50:1) to obtain t-butyl-8-iodooctanoate (5) as a colorless liquid substance (5.53 g, 77%).

Rf=0.47 (silica gel plate, hexane:ethyl acetate=4:1)
IR (KBr) ν cm$^{-1}$: 1730 (—C=O)
$^1$H-NMR (270 MHz, CDCl$_3$)
δ: 3:18 (2H, t, J=7.3 Hz, 8-H$_2$), 2.20 (2H, t, J=7.6 Hz, 2-H$_2$), 1.76-1.87 (2H, complex m, 7-H$_2$), 1.53-1.60 (2H, complex m, 3-H$_2$), 1.44 (9H, s, —C(CH$_3$)$_3$), 1.26-1.41 (6H, complex m, 4-, 5-, 6-H$_2$),
$^{13}$C-NMR (67.5 MHz, CDCl$_3$)
δ: 173.0 (C-1), 79.8 (—C(CH$_3$)$_3$), 35.4 (C-2), 33.3 (C-7), 30.2 (C-8), 29.0 (C-4), 28.7 (C-5), 28.1 (C-6), 28.0 (3C, —C(CH$_3$)$_3$), 24.9 (C-3)
High resolution mass spectrum (EI)
found: m/z: 326.0763 [M]+, calc.: 326.0743 [M], C$_{12}$H$_{23}$O$_2$I

5) Synthesis of (E,E)-1-(1,3-dithian)-2,4-decadiene (7)

1,3-Propanedithiol (18.3 g, 17.0 mL, 169 mmol) and boron trifluoride-diethyl ether complex (3.92 g, 3.40 mL, 27.6 mmol) were added to a dichloromethane solution (140 mL) of 2,4-decadienal (6) (21.4 g, 25.0 mL, 141 mmol) at 0° C. under the argon atmosphere, and the temperature of the reaction solution was raised to room temperature, followed by stirring at room temperature for 12 hours. An aqueous saturated sodium hydrogen carbonate solution (200 mL) was added to stop the reaction, and the mixture was extracted with chloroform (100 mL) three times. The organic layer was washed with saturated brine (100 mL), dried over magnesium sulfate, and concentrated. The resulting brown oily crude product (40 g) was separated and purified by silica gel column chromatography (hexane:ethyl acetate=100:1) to obtain (E,E)-1-(1,3-dithian)-2,4-decadiene (7) as a colorless liquid substance (32.7 g, 96%).

Rf=0.52 (silica gel plate, hexane:ethyl acetate=5:1)
IR (KBr) ν cm$^{-1}$: 1653 (—CH=CH—)
$^1$H-NMR (270 MHz, CDCl$_3$)
δ: 6.34 (1H, dd, J=15.2 Hz, 10.6 Hz, 3-H), 5.99 (1H, dd, J=15.2 Hz, 10.6 Hz, 4-H), 5.73 (1H, dt, J=15.2 Hz, 7.2 Hz, 5-H), 5.59 (1H, dd, J=15.2 Hz, 7.9 Hz, 2-H), 4.66 (1H, d, J=7.9 Hz, 1-H), 2.96-2.79 (4H, complex m, 4'-, 6'-H$_2$), 2.23-2.02 (3H, complex m, 2'-H, 6-H$_2$) 1.91-1.77 (1H, m, 2'-H), 1.39-1.19 (6H, complex m, 7-, 8-, 9-H$_2$), 0.87 (3H, t, J=6.9 Hz, 10-H$_3$)
$^{13}$C-NMR (67.5 MHz, CDCl$_3$)
δ: 137.3 (C-5), 133.9 (C-3), 128.8 (C-4), 126.8 (C-2), 47.6 (C-1), 32.8 (C-6), 31.3 (C-7), 30.2 (C-4', C-6), 29.0 (C-5'), 25.1 (C-8), 22.5 (C-9), 14.0 (C-10)
High resolution mass spectrum (EI)
Found: m/z: 242.1169 [M]+, calc.: 242.1163 [M] (C$_{13}$H$_{22}$O$_2$S$_2$)

6) Synthesis of (E,E)-9-(1,3-dithian)-10,12-octadecadienoic Acid t-butyl Ester (8)

N-butyllithium (1.53 M hexane solution, 612 μL, 0.936 mmol) was added dropwise to a tetrahydrofuran solution (8.5 mL) of (E,E)-1-(1,3-dithian)-2,4-decadiene (7) (200 μL, 206 mg, 0.851 mmol) at −78° C. over 15 minutes under the argon atmosphere, and the mixture was stirred at −78° C. for 1 hour. Thereafter, t-butyl-8-iodooctanoate (5) (327 μL, 416 mg, 1.28 mmol) was added to the reaction solution at once, and the mixture was stirred at −78° C. for 1 hour. An aqueous saturated ammonium chloride solution (10 mL) was added to the reaction solution, the mixture was extracted with ethyl acetate (10 mL) three times, and the organic layer was washed with saturated brine (10 mL) dried over magnesium sulfate, and concentrated. The resulting yellow oily crude product (600 mg) was separated and purified by silica gel column chromatography (hexane:ethyl acetate=100:1) to obtain (E,E)-9-(1, 3-dithian)-10,12-octadecadienoic acid t-butyl ester (8) as a yellow oily substance (318 mg, 85%).

Rf=0.36 (silica gel plate, hexane:ethyl acetate=20:1, developed twice)
IR (KBr) ν cm$^{-1}$: 1730 (—C=O), 1695 (C=C)
$^1$H-NMR (400 MHz, CDCl$_3$)
δ: 6.39 (1H, dd, J=15.2, 10.4 Hz, 11-H), 6.12 (1H, dd, J=14.9, 10.4 Hz, 12-H), 5.76 (1H, dt, J=14.9, 7.2 Hz, 13-H), 5.54 (1H, d, J=15.2 Hz, 10-H), 2.28 (2H, ddd, J=14.0, 11.2, 2.5 Hz, 4'α-, 6'α-H or 4'β-, 6'β-H), 2.64 (2H, ddd, J=14.0, 5.2, 3.0 Hz, 4'α-, 6'α-H or 4'β-, 6'β-H) 2.18 (2H, t, J=7.2 Hz, 2-H$_2$), 2.12-2.06 (2H, m, 14-H$_2$), 2.05-1.98, 1.93-1.91 (1H each, m, 5'-H$_2$), 1.82-1.78 (2H, m, 8-H$_2$), 1.59-1.52 (2H, m, 3-H$_2$), 1.47-1.36 (4H, complex m, 7-, 15-H$_2$), 1.44 (9H, s, —C(CH$_3$)$_3$) 1.34-1.19 (10H, complex m, 4-, 5-, 6-, 16-, 17-H$_2$), 0.89 (3H, t, J=7.1 Hz, 18-H$_3$)
$^{13}$C-NMR (100.6 MHz, CDCl$_3$)
δ: 173.2 (C-1), 135.5 (C-13), 133.8 (C-10), 133.6 (C-11), 129.0 (C-12) 79.8 (—C(CH$_3$)$_3$), 54.9 (C-9), 42.3 (C-8), 35.5 (C-2), 32.6 (C-14), 31.4 (C-16), 29.5 (C-6), 29.0*, 29.0* (*: C-4 and C-5), 28:9 (C-15), 28.1 (3C, —C(CH$_3$)$_3$), 27.2 (3'-C, 6'-C), 25.5 (5'-C), 25.0 (C-3), 23.7 (C-7) 22.5 (C-17), 14.0 (C-18)
High resolution mass spectrum (EI)
Found: m/z: 440.2779 [M]+, calc.: 440.2783 [M] (C$_{25}$H$_{44}$O$_2$S$_2$)

7) Synthesis of (12S,13S)-(E)-12,13-dihydroxy-9-(1, 3-dithian)-10-octadecaenoic Acid t-butyl Ester (9)

AD mix-alpha (1.60 g) was added to a tert-butanol-water solution (1:1) (11.5 mL) at room temperature, the mixture was stirred until it became clear orange, methanesulfonamide (109 mg, 1.15 mmol) was added thereto, and the mixture was stirred until it became uniform. This reaction solution was cooled to 0° C., and stirred vigorously. After the reaction solution became the orange ununiform two-layered solution, (E,E)-9-(1,3-dithian)-10,12-octadecadienoic acid t-butyl ester (8) (528 mg, 1.20 mmol) was added thereto, and the mixture was stirred vigorously at 0° C. for 168 hours. Thereafter, sodium sulfite (500 mg) was added to the reaction solution, the temperature of the mixture was raised to room temperature, the mixture was stirred for 30 minutes and extracted with chloroform (20 mL) three times. The organic layers were combined, washed with saturated brine (20 mL), dried over sodium sulfate, and concentrated. The resulting gray oily crude product (1 g) was separated and purified by silica gel column chromatography (hexane:ethyl acetate=1:1) to obtain (12S,13S)-(E)-12,13-dihydroxy-9-(1,3-dithian)-10-octadecaenoic acid t-butyl ester (9) as a colorless oily substance (237 mg, 55% in view of starting material recovery). In addition, unreacted starting materials were recovered (105 mg, 21%).

Rf=0.38 (silica gel plate, hexane:ethyl acetate=1:1)
[α]$_D^{22}$−4.5°(c 1.60, chloroform)
IR (KBr) ν cm$^{-1}$: 3421 (—OH), 1730 (—C=O), 1628 (—C=C—)
$^1$H-NMR (270 MHz, CDCl$_3$)
δ: 5.91 (1H, dd, J=15.5, 6.6 Hz, 11-H), 5.75 (1H, d, J=15.5 Hz, 10-H) 4.04 (1H, dd, J=6.6, 5.3 Hz, 12-H), 4.01-3.00 (1H, m, 13-H), 2.87 (2H, ddd, J=14.2, 11.5, 2.64 Hz, 4'α-, 6'α-H, or 4'β-, 6'β-H), 2.68-2.63 (2H, m, 4'β-, 6'β-H, or 4'α-, 6'α-H), 2.35 (1H, brs, 12-OH), 2.26 (1H, brs, 13-OH), 2.19 (2H, t, J=7.3 Hz, 2-H$_2$), 2.06-2.01 (2H, m, 5'-H$_2$), 1.93-1.88 (2H, m, 8-H$_2$), 1.67-1.28 (18H, complex m, 3-, 4-, 5-, 6-, 7-, 14-, 15-, 16-, 17-H$_2$), 1.44 (9H, s, —C(CH$_3$)$_3$), 0.89 (3H, t, J=6.6 Hz, 18-H$_3$)

$^{13}$C-NMR (67.5 MHz, CDCl$_3$)

δ: 173.8 (C-1), 136.5 (C-10), 133.6 (C-11), 80.4 (—C(CH$_3$)$_3$), 75.9 (C-12), 75.1 (C-13), 54.7 (C-9), 42.4 (C-8), 35.9 (C-2), 33.5 (C-6) 32.3 (C-14), 29.8 (C-16), 29.4 (C-4 or C-5), 29.3 (C-5 or C-4), 28.5 (3C, —C(CH$_3$)$_3$), 27.5 (C-4', C-6'), 25.8 (C-15), 25.6 (C-5'), 25.4 (C-3) 24.0 (C-7), 22.9 (C-17), 14.4 (C-18)

High resolution mass spectrum (FAB, matrix: NaI)
Found: m/z: 497.2743 [M+Na]$^+$, calc.: 497.2735 [M+Na] (C$_{25}$H$_{46}$O$_4$S$_2$Na)

8) Synthesis of (12S,13S)-(E)-12,13-di-tert-butyldimethylsiloxy-9-(1,3-dithian)10-octadecaenoic Acid t-butyl Ester (10)

2,6-Lutidine (916 μL, 7.87 mmol) was added dropwise to a dichloromethane solution (7.9 mL) of (12S,13S)-(E)-12,13-dihydroxy-9-(1,3-dithian)-10-octadecaenoic acid t-butyl ester (9) (373 mg, 0.787 mmol) at −78° C. under the argon atmosphere and, subsequently, tert-butyldimethylsilyl trifluoromethanesulfonate (901 μL, 0.723 mmol) was added dropwise over 5 minutes, and the mixture was stirred at −78° C. for 10 minutes. Water (1 mL) was added to the reaction solution, the organic layer was taken and extracted with chloroform (10 mL) three times, and the organic layers were combined, washed with saturated brine (10 mL), dried over magnesium sulfate, and concentrated. The resulting brown oily crude product (700 mg) was separated and purified by silica gel column chromatography (hexane:ethyl acetate=100:1) to obtain (12S,13S)-(E)-12,13-di-tert-butyldimethylsiloxy-9-(1,3-dithian)-10-octadecaenoic acid t-butyl ester (10) as a colorless oily substance (489 mg, 89%).

Rf=0.74 (silica gel plate, hexane:ethyl acetate=10:1)
$^1$H-NMR (270 MHz, CDCl$_3$)

δ: 5.97 (1H, dd, J=15.5, 5.0 Hz, 11-H), 5.59 (1H, d, J=15.5 Hz, 10-H) 4.23 (1H, m, 12-H), 3.59 (1H, m, 13-H), 2.98-2.86 (2H, m, 4'α-, 6'α-H, or 4'β-, 6'β-H), 2.67-2.53 (2H, m, 4'β-, 6'β-H, or 4'α-, 6'α-H), 2.18 (2H, t, J=7.6 Hz, 2-H$_2$), 2.05-1.87 (2H, m, 5'-H$_2$), 1.72 (2H, m, 8-H$_2$) 1.70-1.11 (18H, complex m, 3-, 4-, 5-, 6-, 7-, 14-, 15-, 16-, 17-H$_2$) 1.43 (9H, s, —C(CH$_3$)$_3$), 0.91-0.85 (21H, complex m, 18-H$_3$, SiC(CH$_3$)$_3$) 0.11-0.02 (12H, m, —Si(CH$_3$)$_2$)

9) Synthesis of (12S,13S)-(E)-12,13-di-tert-butyldimethylsiloxy-9-oxo-10-octadecaenoic Acid t-butyl Ester (11)

Calcium carbonate (26.7 mg, 0.168 mmol) was added to a tetrahydrofuran (2.6 mL) solution of (12S,13S)-(E)-12,13-di-tert-butyldimethylsiloxy-9-(1,3-dithian)-10-octadecaenoic acid t-butyl ester (10) (93.8 mg, 0.134 mmol) at room temperature, an aqueous solution (520 μL) of mercury (II) perchlorate trihydrate (121 mg, 0.138 mmol) was added dropwise, and the mixture was stirred for 5 minutes. The reaction solution was diluted with ether (1 mL), and suction filtered through a glass filter covered with Celite. The filtrate was concentrated, and the resulting concentrate was dissolved in chloroform (10 mL), washed with saturated brine (5 mL), dried over sodium sulfate, and concentrated. The resulting black oily crude product (85 mg) was separated and purified by silica gel column chromatography (hexane:ethyl acetate=50:1) to obtain (12S,13S)-(E)-12,13-di-tert-butyldimethylsiloxy-9-oxo-10-octadecaenoic acid t-butyl ester (11) as a colorless oily substance (67.4 mg, 83%).

Rf=0.56 (silica gel plate, hexane:ethyl acetate=10:1)
$^1$H-NMR (270 MHz, CDCl$_3$)

δ: 6.96 (1H, dd, J=16.2, 3.6 Hz, 11-H), 6.29 (1H, d, J=16.2 Hz, 10-H), 4.27 (1H, m, 12-H), 3.65 (1H, m, 13-H), 2.54 (2H, t, J=7.3 Hz, 8-H$_2$), 2.19 (2H, t, J=7.6 Hz, 2-H$_2$), 1.66-1.11 (18H, complex m, 3-, 4-, 5-, 6-, 7-, 14-, 15-, 16-, 17-H$_2$), 1.44 (9H, s, —C(CH$_3$)$_3$), 0.96-0.84 (21H, complex m, 18-H$_3$, SiC(CH$_3$)$_3$), 0.11-0.02 (12H, m, —Si(CH$_3$)$_2$)

10) Synthesis of (9S,12S,13S)-(E)-12,13-di-tert-butyldimethylsiloxy-9-hydroxy-10-octadecaenoic Acid t-butyl Ester (12)

(S)-binal-H (0.5 M tetrahydrofuran solution, 335 μL, 0.167 mmol) was added dropwise to a tetrahydrofuran solution (500 μL) of (12S,13S)-(E)-12,13-di-tert-butyldimethylsiloxy-9-oxo-10-octadecaenoic acid t-butyl ester (11) (31.1 mg, 0.0508 mmol) at −78° C. over 5 minutes under the argon atmosphere, and the mixture was stirred at −78° C. for 1 hour. Hydrochloric acid (1.0 N, 1 mL) was added to the reaction solution, the mixture was extracted with chloroform (5 mL) three times, and the organic layer was washed successively with 1.0 N sodium hydroxide (5 mL×3), and saturated brine (5 mL), dried over magnesium sulfate, and concentrated. The resulting colorless oily crude product (32 mg) was separated and purified by silica gel column chromatography (hexane:ethyl acetate=10:1) to obtain (9S,12S,13S)-(E)-12,13-di-tert-butyldimethylsiloxy-9-hydroxy-10-octadecaenoic acid t-butyl ester (12) as a colorless oily substance (31.0 mg, 99%).

Rf=0.29 (silica gel plate, hexane:ethyl acetate=10:1)
$^1$H-NMR (270 MHz, CDCl$_3$)

δ: 5.71 (1H, dd, J=16.2, 4.0 Hz, 11-H), 5.65 (1H, dd, J=15.5, 6.6 Hz, 10-H), 4.16-4.05 (2H, complex m, 9-, 12-H), 3.56-3.53 (1H, m, 13-H), 2.19 (2H, t, J=7.3 Hz, 2-H$_2$), 1.66-1.12 (18H, complex m, 3-, 4-, 5-, 6-, 7-, 14-, 15-, 16-, 17-H$_2$), 1.44 (9H, s, —C(CH$_3$)$_3$), 0.94-0.85 (21H, complex m, 18-H$_3$, SiC(CH$_3$)$_3$), 0.06-0.03 (12H, m, —Si(CH$_3$)$_2$)

11) Synthesis of (9S,12S,13S)-(E)-9,12,13-trihydroxy-10-octadecaenoic Acid t-butyl Ester (13)

Tetrabutylammonium fluoride (1.0 M tetrahydrofuran solution, 420 μL, 0.416 mmol) was added to a tetrahydrofuran solution (500 μL) of (9S,12S,13S)-(E)-12,13-di-tert-butyldimethylsiloxy-9-hydroxy-10-octadecaenoic acid t-butyl ester (12) (11.6 mg, 0.189 mmol) at room temperature, and the mixture was stirred for 3 hours and 25 minutes. The temperature of the reaction solution was raised to 70° C., and the solution was stirred for 1 hour and 30 minutes. The temperature of the reaction solution was returned to room temperature, water (1 mL) was added, the mixture was extracted with chloroform (5 mL) three times, and the organic layer was washed with saturated brine (5 mL) dried over sodium sulfate, and concentrated. The resulting colorless oily crude product (20 mg) was separated and purified by silica gel column chromatography (toluene:ethyl acetate=1:2) to obtain (9S,12S,13S)-(E)-9,12,13-trihydroxy-10-octadecaenoic acid t-butyl ester (13) as a colorless oily substance (6.5 mg, 89%).

Rf=0.32 (silica gel plate, toluene:ethyl acetate=1:2)
$^1$H-NMR (270 MHz, CDCl$_3$)

δ: 5.83 (1H, dd, J=15.8, 5.6 Hz, 10-H), 5.70 (1H, dd, J=15.5, 5.9 Hz, 11-H), 4.15 (1H, m, 9-H), 3.95 (dd, J=6.3, 5.9 Hz, 12-H), 3.55-3.42 (1H, m, 13-H), 2.20 (2H, t, J=7.6 Hz, 2-H$_2$), 1.67-1.18 (18H, complex m, 3-, 4-, 5-, 6-, 7-, 14-, 15-, 16-, 17-H$_2$), 1.44 (9H, s, —C(CH$_3$)$_3$) 0.89 (t, J=6.6 Hz, 18-H$_3$)

12) Synthesis of 9S,12S,13S-trihydroxy-10E-octadecenoic Acid (14)

(9S,12S,13S)-(E)-9,12,13-trihydroxy-10-octadecaenoic acid t-butyl ester (13) (6.5 mg, 0.0168 mmol) was added to an ethanol-water (4:1) solution (500 μL) of 2.0 N potassium hydroxide at room temperature, and the mixture was stirred at room temperature for 46 hours. The reaction solution was cooled to 0° C., 1.0 N hydrochloric acid solution (500 μL) was added to the reaction solution to make it weakly acidic, and the mixture was extracted with chloroform (5 mL) three times. The organic layer was washed with an aqueous saturated sodium hydrogen carbonate solution (5 mL), dried over sodium sulfate, and concentrated. The resulting colorless oily crude product (10 mg) was separated and purified by silica gel column chromatography (chloroform:methanol=10:1) to obtain 9S,12S,13S-trihydroxy-10E-octadecenoic acid (14) as a while solid (4.5 mg, 82%).

Rf=0.24 (silica gel plate, chloroform:methanol:acetic acid=10:1:0.1)

$[\alpha]_D^{25}$ −8.0°(c 0.30, methanol)

$^1$H-NMR (400 MHz, CD$_3$OD)

δ: 5.72 (1H, dd, J=15.9, 5.7 Hz, 10-H), 5.67 (1H, dd, J=15.9, 5.3 Hz, 11-H), 4.05 (1H, m, 9-H), 3.91 (1H, dd, J=5.7, 5.3 Hz, 12-H), 3.41 (1H, ddd, J=8.1, 5.7, 2.1 Hz, 13-H), 2.28 (2H, t, J=7.6 Hz, 2-H$_2$), 1.60 (2H, dt, J=7.6, 6.9 Hz, 3-H$_2$), 1.57-1.44 (2H, m, 8-H$_2$), 1.24-1.54 (16H, m, 4-, 5-, 6-, 7-, 14-, 15-, 16-, 17-H$_2$), 0.91 (3H, t, J=6.3 Hz, 18-H$_3$)

$^{13}$C-NMR (100 MHz, CD$_3$OD)

δ: 177.7 (C-1), 136.5 (C-11), 131.1 (C-10), 76.5 (C-12), 75.8 (C-13) 73.0 (C-9), 38.3 (C-8), 35.0 (C-2), 33.6 (C-14), 33.1 (C-16), 30.5*, 30.4*, 30.2* (*: C-4 or C-5 or C-6), 26.6 (C-15), 26.4 (C-7), 26.1 (C-3) 23.7 (C-17), 14.4 (C-18)

Example 4

Synthesis of 9S,12R,13S-trihydroxy-10E-octadecenoic Acid (20)

Outline of a process for synthesizing 9S,12R,13S-trihydroxy-10E-octadecenoic acid is shown in Scheme 3.

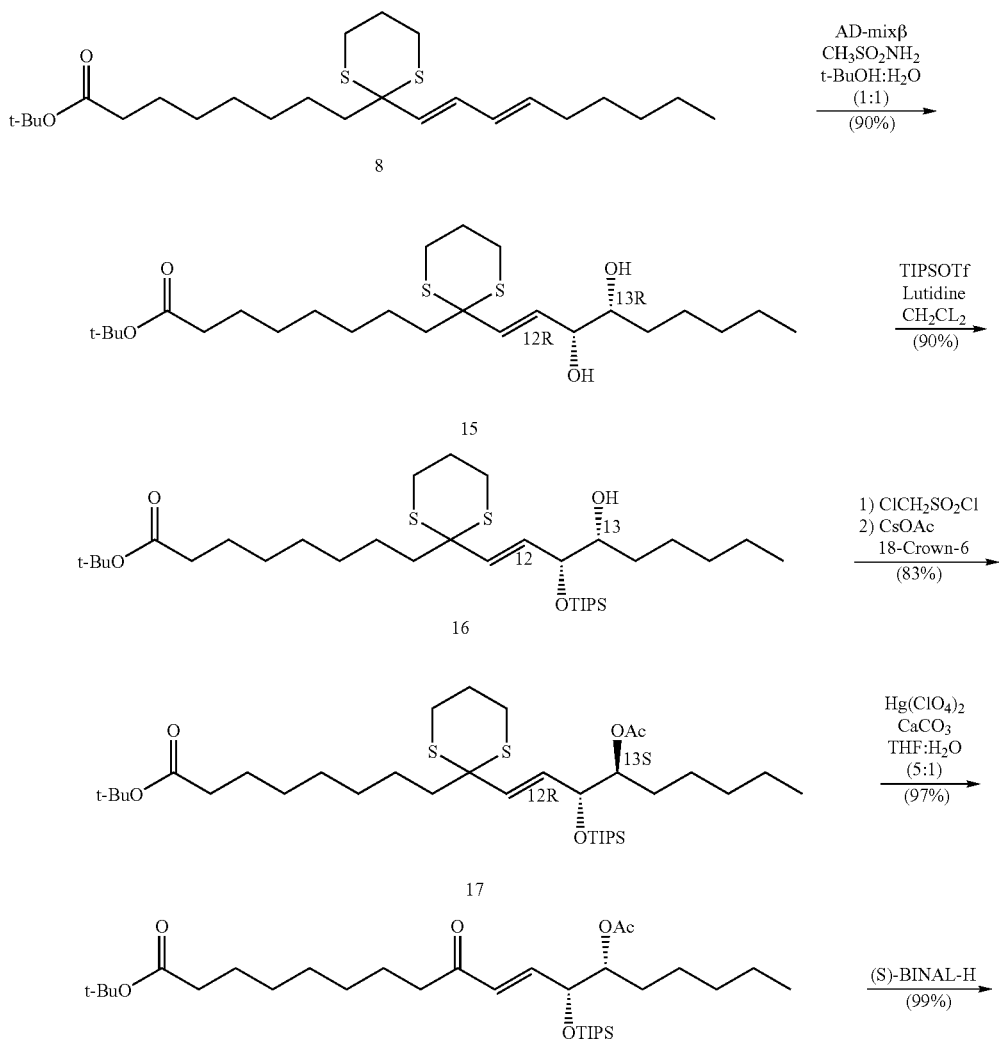

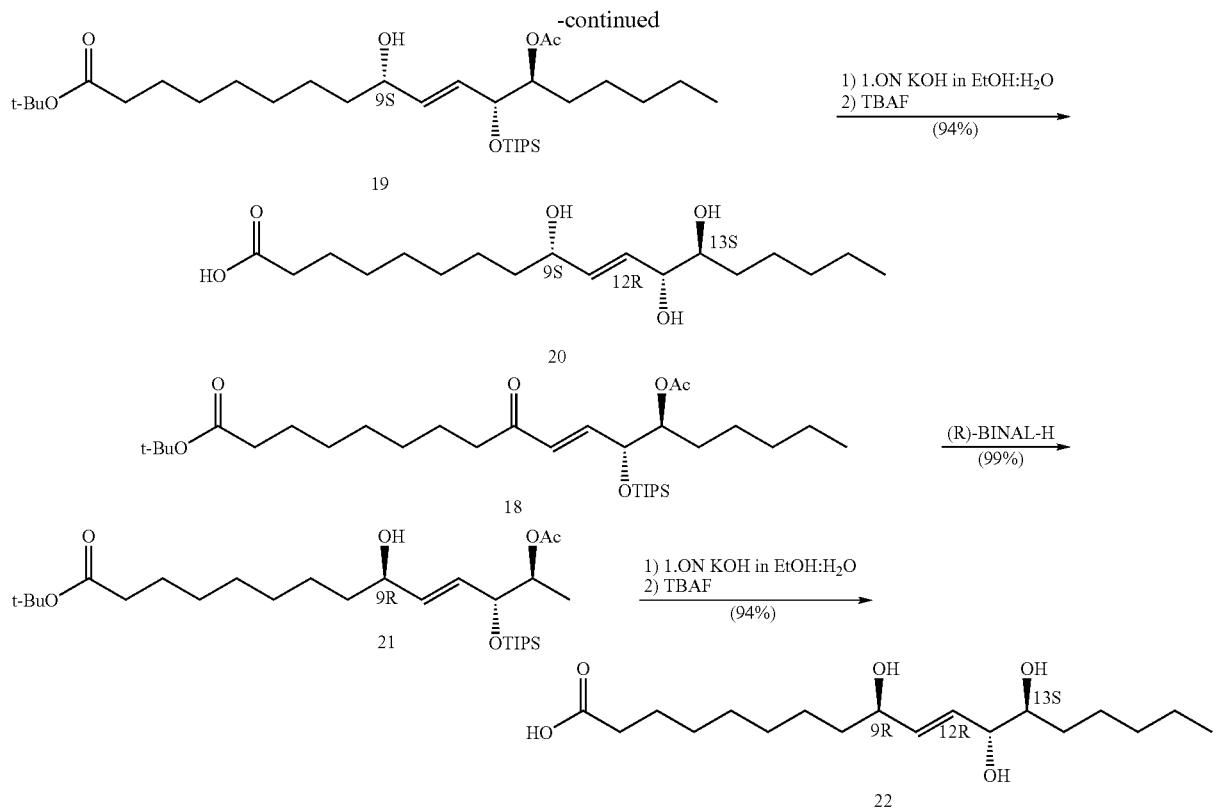

1) Synthesis of (12R,13R)-(E)-12,13-dihydroxy-9-(1,3-dithian)-10-octadecaenoic Acid t-butyl Ester (15)

AD mix-beta (1.68 g) was added to a tert-butanol-water solution (1:1) (12 mL) at room temperature, the mixture was stirred until it became clear orange, methanesulfonamide (114 mg, 1.20 mmol) was added, and the mixture was stirred until it became uniform. The reaction solution was cooled to 0° C. and stirred vigorously. After the reaction solution became the orange ununiform two-layered solution, (E,E)-9-(1,3-dithian)-10,12-octadecadienoic acid t-butyl ester (8) (528 mg, 1.20 mmol) synthesized in Example 3-6) was added, and the mixture was stirred vigorously at 0° C. for 73 hours. Thereafter, sodium sulfite (500 mg) was added to the reaction solution, and the temperature of the solution was raised to room temperature. The mixture was stirred for 30 minutes and extracted with chloroform (20 mL) three times. The organic layers were combined, washed with saturated brine (20 mL), dried over magnesium sulfate, and concentrated. The resulting gray oily crude product (1 g) was separated and purified by silica gel column chromatography (hexane:ethyl acetate=1:1) to obtain (12R,13R)-(E)-12,13-dihydroxy-9-(1,3-dithian)-10-octadecaenoic acid t-butyl ester (15) as a colorless oily substance (388 mg, 90% in view of starting material recovery). In addition, unreacted starting materials were recovered (127 mg, 24%).

Rf=0.38 (silica gel plate, hexane:ethyl acetate=1:1)

$[\alpha]_D^{24}$ +5.2° (c 1.08, chloroform)

IR (KBr) ν cm$^{-1}$: 3421 (—OH), 17.30 (—C=O), 1628 (—C=C—)

$^1$H-NMR (270 MHz, CDCl$_3$)

δ: 5.91 (1H, dd, J=15.5, 6.6 Hz, 11-H), 5.75 (1H, d, J=15.5 Hz, 10-H), 4.04 (1H, dd, J=6.6, 5.3 Hz, 12-H), 4.01-3.00 (1H, m, 13-H), 2.87 (2H, ddd, J=14.2, 11.5, 2.64 Hz, 4'α-, 6'α-H, or 4'β-, 6'β-H), 2.68-2.63 (2H, m, 4'β-, 6'β-H, or 4'α-, 6'α-H), 2.35 (1H, brs, 12-OH), 2.26 (1H, brs, 13-OH), 2.19 (2H, t, J=7.3 Hz, 2-H$_2$), 2.06-2.01 (2H, m, 5'-H$_2$), 1.93-1.88 (2H, m, 8-H$_2$), 1.67-1.28 (18H, complex m, 3-, 4-, 5-, 6-, 7-, 14-, 15-, 16-, 17-H$_2$), 1.44 (9H, s, —C(CH$_3$)$_3$), 0.89 (3H, t, J=6.6 Hz, 18-H$_3$)

$^{13}$C-NMR (67.5 MHz, CDCl$_3$)

δ: 173.8 (C-1), 136.5 (C-10), 133.6 (C-11), 80.4 (—C(CH$_3$)$_3$), 75.9 (C-12), 75.1 (C-13), 54.7 (C-9), 42.4 (C-8), 35.9 (C-2), 33.5 (C-6), 32.3 (C-14), 29.8 (C-16), 29.4 (C-4 or C-5), 29.3 (C-5 or C-4), 28.5 (3C, —C(CH$_3$)$_3$), 27.5 (C-4', C-6'), 25.8 (C-15), 25.6 (C-5'), 25.4 (C-3) 24.0 (C-7), 22.9 (C-17), 14.4 (C-18)

High resolution mass spectrum (FAB, matrix: NaI)

Found: m/z: 497.2740 [M+Na]$^+$, calc.: 497.2735 [M+Na] (C$_{25}$H$_{46}$O$_4$S$_2$Na)

2) Synthesis of (12R,13R)-(E)-9-(1,3-dithian)-13-hydroxy-12-triisopropylsiloxy-10-octadecaenoic Acid t-butyl Ester (16)

2,6-Lutidine (160 μL, 1.38 mmol) was added dropwise to a dichloromethane solution (14 mL) of (12R,13R)-(E)-12,13-dihydroxy-9-(1,3-dithian)-10-octadecaenoic acid t-butyl ester (15) (326 mg, 0.689 mmol) at −78° C. under the argon atmosphere. Subsequently, triisopropylsilyl trifluoromethanesulfonate (194 μL, 0.723 mmol) was added dropwise over 20 minutes, and the mixture was stirred at −78° C. for 8 hours. After water (1 mL) was added to the reaction solution, the organic layer was taken and extracted with chloroform (10 mL) three times. The organic layers were combined, washed with saturated brine (10 mL), dried over magnesium sulfate, and concentrated. The resulting green oily crude product (500 mg) was separated and purified by silica gel column chromatography (hexane:ethyl acetate=50:1) to obtain (12R,13R)-(E)-9-(1,3-dithian)-13-hydroxy-12-triisopropylsiloxy-10-octadecaenoic acid t-butyl ester (16) as a colorless oily substance (391 mg, 90%).

Rf=0.44 (silica gel plate, hexane:ethyl acetate=5:1)

$[\alpha]_D^{24}$ -4.8° (c 1.01, chloroform)

IR (KBr) ν cm$^{-1}$: 3442 (—OH), 1731 (—C=O), 1630 (—C=C—)

$^1$H-NMR (270 MHz, CDCl$_3$)

δ: 5.91 (1H, dd, J=15.5, 7.6 Hz, 11-H), 5.68 (1H, d, J=15.5 Hz, 10-H) 4.16 (1H, dd, J=7.6, 6.9 Hz, 12-H), 4.01-3.00 (1H, m, 13-H), 2.92-2.77 (2H, m, 4'α-, 6'α-H, or 4'β-, 6'β-H), 2.69-2.63 (2H, m, 4'β-, 6'β-H, or 4'α-, 6'α-H) 2.18 (2H, t, J=7.3 Hz, 2-H$_2$), 2.11-1.87 (2H, m, 5'-H$_2$), 1.83-1.67 (2H, m, 8-H$_2$), 1.67-1.58 (18H, complex m, 3-, 4-, 5-, 6-, 7-, 14-, 15-, 16-, 17-H$_2$), 1.42 (9H, s, —C(CH$_3$)$_3$), 1.15-1.02 (21H, m, —Si(CH(CH$_3$)$_2$)$_3$), 0.89 (3H, t, J=6.6 Hz, 18-H$_3$)

$^{13}$C-NMR (67.5 MHz, CDCl$_3$)

δ: 173.2 (C-1), 135.7 (C-10), 133.7 (C-11), 79.9 (—C(CH$_3$)$_3$), 77.3 (C-12), 75.5 (C-13), 54.2 (C-9), 42.2 (C-8), 35.5 (C-2), 32.6 (C-6), 31.9 (C-14), 29.7 (C-16), 29.6 (C-15), 29.1 (C-4 or C-5), 29.0 (C-5 or C-4), 28.0 (—C(CH$_3$)$_3$), 27.0 (C-4' or C-6'), 26.9 (C-4' or C-6'), 25.7 (C-5'), 25.5 (C-3), 23.9 (C-7), 22.6 (C-17), 18.1 (—Si(CH(CH$_3$)$_2$)$_3$) 14.0 (C-18), 12.5 (—Si(CH(CH$_3$)$_2$)$_3$)

High resolution mass spectrum (FAB, matrix: NaI)

Found: m/z: 653.4061 [M+Na]$^+$, calc.: 653.4070 [M+Na] (C$_{34}$H$_{66}$O$_4$SiS$_2$Na)

3) Synthesis of (12R,13S)-(E)-13-acetoxy-9-(1,3-dithian)-12-triisopropylsiloxy-10-octadecaenoic Acid t-butyl Ester (17)

Monochloromethanesulfonyl chloride (3.9 μL, 0.030 mmol) was added dropwise to a pyridine solution (0.5 mL) of (12R,13R)-(E)-9-(1,3-dithian)-13-hydroxy-12-triisopropylsiloxy-10-octadecaenoic acid t-butyl ester (16) (13.0 mg, 0.021 mmol) at 0° C. under the argon atmosphere, and the mixture was stirred at 0° C. for 2 hours. Water (0.5 mL) was added to the reaction solution, the mixture was extracted with chloroform (5 mL) three times. The organic layers were combined, washed with saturated brine (5 mL), dried over magnesium sulfate, and concentrated. The resulting black oily crude product (15.2 mg) was dissolved in a benzene solution (1.0 mL) at room temperature under the argon atmosphere, cesium acetate (19.8 mg, 0.10 mmol) and 18-crown-6 (4.1 mg, 0.021 mmol) were successively added to the solution, and the mixture was heated under reflux at 80° C. for 20 hours. The temperature of the reaction solution was returned to room temperature, water (500 μL) was added, and the mixture was extracted with chloroform (5 mL) three times. The organic layer was washed with saturated brine (5 mL), dried over magnesium sulfate, and concentrated. The resulting black oily crude product (30 mg) was separated and purified by silica gel column chromatography (hexane:ethyl acetate=50:1) to obtain (12R,13S)-(E)-13-acetoxy-9-(1,3-dithian)-12-triisopropylsiloxy-10-octadecaenoic acid t-butyl ester (17) as a colorless oily substance (11.5 mg, 83%).

Rf=0.50 (silica gel plate, hexane:ethyl acetate=8:1)

$[\alpha]_D^{24}$ -21.8°(c 0.87, chloroform)

IR (KBr) ν cm$^{-1}$: 1734 (—C=O), 1635 (—C=C—)

$^1$H-NMR (270 MHz, CDCl$_3$)

δ: 5.89 (1H, dd, J=15.5, 6.3 Hz, 11-H), 5.69 (1H, d, J=15.5 Hz, 10-H), 4.95-4.89 (1H, m, 13-H), 4.47 (1H, dd, J=6.3, 2.6 Hz, 12-H), 2.93-2.79 (2H, m, 4'α-, 6'α-H, or 4'β-, 6'β-H), 2.69-2.61 (2H, m, 4'β-, 6'β-H, or 4'α-, 6'α-H) 2.18 (2H, t, J=7.3 Hz, 2-H$_2$), 2.05 (3H, s, —COCH$_3$) 2.02-1.87 (2H, m, 5'-H$_2$), 1.83-1.66 (2H, m, 8-H$_2$), 1.47-1.15 (18H, complex m, 3-, 4-, 5-, 6-, 7-, 14-, 15-, 16-, 17-H$_2$), 1.43 (9H, s, —C(CH$_3$)$_3$), 1.10-0.95 (21H, m, —Si(CH(CH$_3$)$_2$)$_3$), 0.87 (3H, t, J=6.9 Hz, 18-H$_3$)

$^{13}$C-NMR (67.5 MHz, CDCl$_3$)

δ: 173.2 (C-1), 170.8 (—COCH$_3$), 135.0 (C-10), 133.1 (C-11), 79.9 (—C(CH$_3$)$_3$), 77.4 (C-12), 77.2 (C-13), 54.3 (C-9), 42.2 (C-8), 35.5 (C-2), 31.7 (C-14), 29.6 (C-16), 29.1*, 29.0 *, 29.0* (*: C-4 or C-5 or C-6), 28.1 (—C(CH$_3$)$_3$), 27.0 (C-4' or C-6'), 26.9 (C-4' or C-6'), 25.5 (C-5'), 25.3 (C-3), 25.0 (C-15), 23.8 (C-7), 22.4 (C-17), 21.2 (—COCH$_3$) 18.0 (—Si(CH(CH$_3$) 2)$_3$), 14.0 (C-18), 12.5 (—Si(CH(CH$_3$)$_2$)$_3$)

High resolution mass spectrum (FAB, matrix: NaI)

Found: m/z: 695.4162 [M+Na]$^+$, calc.: 695.4175 [M+Na] (C$_{36}$H$_{68}$O$_5$SiS$_2$Na)

4) Synthesis of (12R, 13S)-(E)-13-acetoxy-9-oxo-12-triisopropylsiloxy-10-octadecaenoic Acid t-butyl Ester (18)

Calcium carbonate (90.4 mg, 0.904 mmol) was added to a tetrahydrofuran solution (4.5 mL) of (12R,13S)-(E)-13-acetoxy-9-(1,3-dithian)-12-triisopropylsiloxy-10-octadecaenoic acid t-butyl ester (17) (304 mg, 0.452 mmol) at room temperature, and an aqueous solution (900 μL) of mercury (II) perchlorate trihydrate (410 mg, 0.904 mmol) was added dropwise to the mixture, followed by stirring for 5 minutes. The reaction solution was diluted with ether (2 mL), and suction filtered through a glass filter covered with Celite. The filtrate was concentrated, the resulting concentrate was dissolved in chloroform (15 mL), and the solution was washed with saturated brine (5 mL), dried over sodium sulfate, and concentrated. The resulting black oily crude product (300 mg) was separated and purified by silica gel column chromatography (hexane:ethyl acetate=10:1) to obtain (12R, 13S)-(E)-13-acetoxy-9-oxo-12-triisopropylsiloxy-10-octadecaenoic acid t-butyl ester (18) as a colorless oily substance (250 mg, 97%).

Rf=0.55 (silica gel plate, hexane:ethyl acetate=6:1)

$[\alpha]_D^{24}$ -22.0°(c 0.98, chloroform)

IR (KBr) ν cm$^{-1}$: 1735 (—C=O, ester), 1680 (—C=O, ketone), 1633 (—C=C—)

$^1$H-NMR (270 MHz, CDCl$_3$)

δ: 6.71 (1H, dd, J=15.8, 5.9 Hz, 11-H), 6.24 (1H, d, J=15.8 Hz, 10-H) 4.93 (1H, m, 13-H), 4.48 (1H, dd, J=5.9, 3.6 Hz, 12-H), 2.55 (2H, t, J=7.6 Hz, 8-H$_2$), 2.19 (2H, t, J=7.3 Hz, 2-H$_2$), 2.04 (3H, s, —COCH$_3$), 1.73-1.17 (18H, complex m, 3-, 4-, 5-, 6-, 7-, 14-, 15-, 16-, 17-H$_2$), 1.44 (9H, s, —C(CH$_3$)$_3$), 1.12-0.98 (21H, m, —Si(CH(CH$_3$)$_2$)$_3$), 0.87 (3H, t, J=6.3 Hz, 18-H$_3$)

$^{13}$C-NMR (67.5 MHz, CDCl$_3$)

δ: 200.3 (C-9), 173.2 (C-1), 170.6 (—COCH$_3$), 144.6 (C-11), 130.5 (C-10) 79.8 (—C(CH$_3$)$_3$), 76.4 (C-12), 74.2 (C-13), 40.2 (C-8), 35.5 (C-2), 31.4 (C-6), 31.5 (C-14), 29.0*, 29.0*, 28.9*, 28.9* (*: C-4 or C-5 or C-6 or C-16), 28.0 (—C(CH$_3$)$_3$), 25.2 (C-3), 24.9 (C-15), 24.1 (C-7), 22.4 (C-17), 21.0 (—COCH$_3$), 17.9 (—Si(CH(CH$_3$)$_2$)$_3$), 13.9 (C-18), 12.3 (—Si (CH(CH$_3$)$_2$)$_3$)

High resolution mass spectrum (FAB, matrix: NaI)

Found: m/z: 605:4202 [M+Na]$^+$, calc.: 605.4213 [M+Na] (C$_{33}$H$_{62}$O$_6$SiNa)

5) Synthesis of (9S,12R,13S)-(E)-13-acetoxy-9-hydroxy-12-triisopropylsiloxy-10-octadecaenoic Acid t-butyl Ester (19)

(S)-binal-H (0.5 M tetrahydrofuran solution, 215 μl, 0.107 mmol) was added dropwise to a tetrahydrofuran solution (300 μl) of (12R,13S)-(E)-13-acetoxy-9-oxo-12-triisopropylsiloxy 10-octadecaenoic acid t-butyl ester (18) (18.7 mg, 0.033 mmol) at −78° C. over 5 minutes under the argon atmosphere, and the mixture was stirred at −78° C. for 1 hour and 30 minutes. Hydrochloric acid (1.0 N, 1 mL) was added to the reaction solution, and the mixture was extracted with chloroform (5 mL) three times. The organic layer was washed successively with 1.0 N sodium hydroxide (5 mL) and saturated brine (5 mL), dried over sodium sulfate, and concentrated. The resulting colorless oily crude product (20 mg) was separated and purified by silica gel column chromatography (hexane:ethyl acetate=10:1) to obtain (9S,12R,13S)-(E)-13-acetoxy-9-hydroxy-12-triisopropylsiloxy-10-octadecaenoic acid t-butyl ester (19) as a colorless oily substance (18.6 mg, 99%).

Rf=0.44 (silica gel plate, hexane:ethyl acetate=4:1)
$[\alpha]_D^{25}$ −18.9° (c 1.40, chloroform)
IR (KBr) ν cm$^1$: 1733 (—C=O), 1630 (—C=C—)
$^1$H-NMR (270 MHz, CDCl$_3$)
δ: 5.69 (1H, dd, J=15.8, 5.6 Hz, 10-H), 5.62 (1H, dd, J=15.8, 5.9 Hz, 11-H), 4.93 (1H, m, 13-H), 4.29 (1H, dd, J=5.9, 3.0 Hz, 12-H), 4.11-4.07 (1H, m, 9-H), 2.19 (2H, t, J=7.3 Hz, 2-H$_2$), 2.03 (3H, s, —COCH$_3$), 1.79-1.20 (20H, complex m, 3-, 4-, 5-, 6-, 7-, 8-, 14-, 15-, 16-, 17-H$_2$), 1.44 (9H, s, —C(CH$_3$)$_3$), 1.10-0.98 (21H, m, —Si(CH(CH$_3$)$_2$)$_3$) 0.87 (3H, t, J=6.3 Hz, 18-H$_3$)
$^{13}$C-NMR (67.5 MHz, CDCl$_3$)
δ: 173.2 (C-1), 170.8 (—COCH$_3$), 135.2 (C-11), 130.2 (C-10), 79.9 (—C(CH$_3$)$_3$), 77.1 (C-13), 74.8 (C-12), 72.2 (C-9), 37.1 (C-8), 35.5 (C-2), 31.5 (C-14), 29.3*, 29.2* (*: C-4 or C-5), 29.0, 28.9 (**: C-6 or C-16), 28.1 (—C(CH$_3$)$_3$), 25.3 (C-3), 25.2 (C-15), 25.0 (C-7), 22.5 (C-17), 21.2 (—COCH$_3$), 18.0 (—Si(CH(CH$_3$)$_2$)$_3$), 14.0 (C-18), 12.4 (—Si (CH(CH$_3$)$_2$)$_3$)
High resolution mass spectrum (FAB, matrix: NaI)
Found: m/z: 607.4372 [M+Na]$^+$, calc.: 607.4370 [M+Na] (C$_{33}$H$_{64}$O$_6$SiNa)

6) Synthesis of 9S,12R,13S-trihydroxy-10E-octadecenoic Acid (20)

(9S,12R,13S)-(E)-13-acetoxy-9-hydroxy-12-triisopropylsiloxy-10-octadecaenoic acid t-butyl ester (19) (17.2 mg, 29.8 μmol) was added to an ethanol-water (4:1) solution (500 μL) of 0.1 N potassium hydroxide at room temperature, and the mixture was stirred at room temperature for 120 hours. The reaction solution was cooled to 0° C., a 1.0 N hydrochloric acid solution (500 μL) was added to the reaction solution to make it weakly acidic, the mixture was extracted with chloroform (5 mL) three times, and the organic layer was washed with saturated sodium hydrogen carbonate (5 mL), dried over sodium sulfate, and concentrated. The resulting colorless oily crude product (15.2 mg) was dissolved in a tetrahydrofuran (1.0 mL), tetrabutylammonium fluoride (1.0 M tetrahydrofuran solution, 30 μL, 29.8 μmol) was added to the solution at 0° C., and the temperature of the mixture was raised to room temperature, followed by stirring for 52 hours. An aqueous saturated ammonium chloride solution (500 μL) was added, the mixture was extracted with ethyl acetate (5 mL) three times, and the organic layer was washed with saturated brine (5 mL), dried over sodium sulfate, and concentrated. The resulting black oily crude product (25 mg) was separated and purified by silica gel column chromatography (ethyl acetate) to obtain 9S,12R,13S-trihydroxy-10E-octadecenoic acid (20) as a white solid (9.3 mg, 94%).

Rf=0.23 (silica gel plate, chloroform:methanol:acetic acid=10:1:0.1)
mp: 67-70° C. (methanol)
$[\alpha]_D^{28}$ +7.8°(c 0.18, methanol)
IR (KBr) ν cm$^{-1}$: 3421 (—OH), 1699 (—C=O), 1637 (—C=C—)
$^1$H-NMR (400 MHz, CD$_3$OD)
δ: 5.66 (1H, dd, J=15.8, 6.0 Hz, 10-H), 5.72 (1H, dd, J=15.8, 5.5 Hz, 11-H), 4.04 (1H, ddd, J=6.5, 6.0, 5.0 Hz, 9-H), 3.91 (1H, dd, J=5.5, 4.5 Hz, 12-H), 3.49 (1H, ddd, J=7.5, 4.5, 2.0 Hz, 13-H), 2.27 (2H, t, J=7.5 Hz, 2-H$_2$), 1.60 (2H, dt, J=7.6, 6.9 Hz, 3-H$_2$), 1.57-1.44 (2H, m, 8-H$_2$), 1.24-1.54 (16H, m, 4-, 5-, 6-, 7-, 14-, 15-, 16-, 17-H$_2$), 0.91 (3H, t, J=6.3 Hz, 18-H$_3$)
$^{13}$C-NMR (100 MHz, CD$_3$OD)
δ: 177.8 (C-1), 136.7 (C-11), 130.9 (C-10), 76.6 (C-12), 75.7 (C-13) 73.3 (C-9), 38.4 (C-8), 35.1 (C-2), 33.7 (C-14), 33.1 (C-16), 30.6*, 30.4* (*:C-4 or C-5), 30.2 (C-6), 26.7 (C-15), 26.5 (C-7), 26.1 (C-3) 23.7 (C-17), 14.4 (C-18)
High resolution mass spectrum (FAB, matrix: NBA)
Found: m/z: 353.2307 [M+Na]$^+$, calc.: 353.2304 [M+Na] (C$_{18}$H$_{34}$O$_5$Na)

Example 5

Synthesis of 9R,12R,13S-trihydroxy-10E-octadecenoic Acid (22)

Outline of a process for synthesizing 9R,12R,13S-trihydroxy-10E-octadecenoic acid is shown in Scheme 3.

1) Synthesis of (9R,12R,13S)-(E)-13-acetoxy-9-hydroxy-12-triisopropylsiloxy-10-octadecaenoic Acid t-butyl Ester (21)

(R)-binal-H (0.5 M tetrahydrofuran solution, 232 μL, 0.116 mmol) was added dropwise to a tetrahydrofuran solution (0.35 mL) of (12R,13S)-(E)-13-acetoxy-9-oxo-12-triisopropylsiloxy-10-octadecaenoic acid t-butyl ester (18) (20.5 mg, 0.0352 mmol) synthesized in Example 4-4) at −78° C. over 5 minutes under the argon atmosphere, and the mixture was stirred at −78° C. for 1 hour. Hydrochloric acid (1.0 N, 1 mL) was added to the reaction solution, and the mixture was extracted with chloroform (5 mL) three times. The organic layers were combined, washed successively with 1.0 N sodium hydroxide (5 mL×3) and saturated brine (5 mL), dried over sodium sulfate, and concentrated. The resulting colorless oily crude product (21 mg) was separated and purified by silica gel column chromatography (hexane:ethyl acetate=10:1) to obtain (9R,12R,13S)-(E)-13-acetoxy-9-hydroxy-12-triisopropylsiloxy-10-octadecaenoic acid t-butyl ester (21) (20.3 mg, 99%)

Rf=0.43 (silica gel plate, hexane:ethyl acetate=4:1)
IR (KBr) ν cm$^{-1}$: 3439 (—OH), 1734 (—C=O), 1640 (—C=C—)
$^1$H-NMR (270 MHz, CDCl$_3$)
δ: 5.71 (2H, m, 10, 11-H), 4.86 (1H, m, 13-H), 4.28 (1H, dd, J=5.3, 4.0 Hz, 12-H), 4.13-4.07 (1H, m, 9-H), 2.19 (2H, t, J=7.3 Hz, 2-H$_2$), 2.04 (3H, s, —COCH$_3$), 1.79-1.20 (18H, complex m, 3-, 4-, 5-, 6-, 7-, 14-, 15-, 16-, 17-H$_2$), 1.44 (9H, s, —C(CH$_3$)$_3$), 1.10-0.98 (21H, m, —Si(CH(CH$_3$)$_2$)$_3$), 0.87 (3H, t, J=6.3 Hz, 18-H$_3$)
$^{13}$C-NMR (67.5 MHz, CDCl$_3$)

δ: 173.3 (C-1), 170.9 (—$\underline{C}$OCH$_3$), 135.2 (C-11), 130.5 (C-10), 79.9 (—$\underline{C}$(CH$_3$)$_3$), 77.2 (C-13), 74.8 (C-12), 72.2 (C-9), 37.1 (C-8), 35.5 (C-2), 31.7 (C-14), 29.4*, 29.3* (*: C-4 or C-5), 29.0 , 29.0 (**: C-6 or C-16), 28.0 (—C(CH$_3$)$_3$), 25.3 (C-3, C-15), 25.0 (C-7), 21.2 (C-17), 21.2 (—COCH$_3$), 18.0 (—Si(CH($\underline{C}$H$_3$)$_2$)$_3$), 14.0 (C-18), 12.4 (—Si($\underline{C}$H(CH$_3$) 2) 3)

2) Synthesis of 9R,12R,13S-trihydroxy-10E-octadecenoic Acid (22)

(9R,12R,13S)-(E)-13-acetoxy-9-hydroxy-12-triisopropylsiloxy-10-octadecaenoic acid t-butyl ester (21) (26.5 mg, 0.0454 mmol) was added to an ethanol-water (4:1) solution (0.5 mL) of 0.1 N potassium hydroxide at room temperature, and the mixture was stirred at room temperature for 120 hours. The reaction solution was cooled to 0° C., a 1.0 N hydrochloric acid solution (0.5 mL) was added to the reaction solution to make it weakly acidic, the mixture was extracted with chloroform (5 mL) three times, and the organic layer was washed with saturated sodium hydrogen carbonate (5 mL), dried over sodium sulfate, and concentrated. The resulting colorless oily crude product (30 mg) was dissolved in a tetrahydrofuran (0.5 mL), tetrabutylammonium fluoride (1.0 M tetrahydrofuran solution, 45.4 μL, 0.0454 mmol) was added to the solution at 0° C., and the temperature of the mixture was raised to room temperature, followed by stirring for 45 hours. An aqueous saturated ammonium chloride solution (1.0 mL) was added, the mixture was extracted with ethyl acetate (10 mL) three times, and the organic layer was washed with saturated brine (5 mL), dried over sodium sulfate, and concentrated. The resulting colorless oily crude product (40 mg) was separated and purified by silica gel column chromatography (ethyl acetate) to obtain 9R,12R,13S-trihydroxy-10E-octadecenoic acid (22) as a white solid (14.0 mg, 94%).

Rf=0.24 (silica gel plate, chloroform:methanol:acetic acid=10:1:0.1)

$[\alpha]_D^{29}$ −5.3 (c 0.15, methanol)

IR (KBr) ν cm$^{-1}$: 3420 (—OH), 1701 (—C=O), 1637 (—C=C—)

$^1$H-NMR (400 MHz, CD$_3$OD)

δ: 5.68 (1H, dd, J=15.9, 5.5 Hz, 10-H), 5.73 (1H, dd, J=15.9, 5.0 Hz, 11-H), 4.05 (1H, ddd, J=6.0, 5.5, 5.0 Hz, 9-H), 3.93 (1H, dd, J=5.0, 4.5 Hz, 12-H), 3.47 (1H, ddd, J=8.5, 4.5, 2.1 Hz, 13-H), 2.27 (2H, t, J=7.5 Hz, 2-H$_2$), 1.60 (2H, dt, J=7.6, 7.0 Hz, 3-H$_2$) 1.57-1.44 (2H, m, 8-H$_2$), 1.24-1.54 (16H, m, 4-, 5-, 6-, 7-, 14-, 15-, 16-, 17-H$_2$), 0.91 (3H, t, J=6.3 Hz, 18-H$_3$)

$^{13}$C-NMR (100 MHz, CD$_3$OD)

δ: 177.7 (C-1), 136.5 (C-11), 130.5 (C-10), 76.5 (C-12), 75.7 (C-13) 73.0 (C-9), 38.3 (C-8), 34.9 (C-2), 33.5 (C-14), 33.1 (C-16), 30.5*, 30.3* (*: C-4 or C-5), 30.2 (C-6), 26.7 (C-15), 26.4 (C-7), 26.1 (C-3) 23.7 (C-17), 14.4 (C-18)

$^1$H-NMRs for these synthesized three kinds of hydroxy unsaturated fatty acids and hydroxy unsaturated fatty acid of the present invention purified from Pinelliae Tuber are shown in FIG. 1. These hydroxy unsaturated fatty acids can be clearly distinguished from each other by the shape of a coupling signal of the protons at 10 and 11-positions and chemical shift of the proton at 13-position.

Retention times in high performance liquid chromatography of these synthesized three kinds of hydroxy unsaturated fatty acids and hydroxy unsaturated fatty acid of the present invention purified from Pinelliae Tuber are shown in Table 1. 9S,12S,13S-trihydroxy-10E-octadecenoic acid was eluted at a retention time clearly distinguishable from other two kinds of hydroxy unsaturated fatty acids, 9S,13S-trihydroxy-10E-octadecenoic acid and 9R,12R,13S-trihydroxy-10E-octadecenoic acid, while 9S,12S,13S-trihydroxy-10E-octadecenoic acid and 9R,12R,13S-trihydroxy-10E-octadecenoic acid were eluted at close retention times.

TABLE 1

Retention time of hydroxy unsaturated fatty acid from high performance liquid chromatography

| Hydroxy unsaturated fatty acid | Retention time (min) |
|---|---|
| 9S,12S,13S-trihydroxy-10E-octadecenoic acid | 4.101 |
| 9S,12R,13S-trihydroxy-10E-octadecenoic acid | 4.356 |
| 9R,12R,13S-trihydroxy-10E-octadecenoic acid | 4.006 |

High performance liquid chromatography conditions:
Column: Pegasil (4.6 mm i.d.×150 mm, Senshu Scientific Co., Ltd.)
Solvent: 0.01% acetic acid-containing 70% methanol
Flow rate: 1 mL/min
Detector: ultraviolet detector (210 nm)

It was confirmed by the known biological method that the above-mentioned 9S,12S,13S-trihydroxy-10E-octadecenoic acid, 9S,12R,13S-trihydroxy-10E-octadecenoic acid, or 9R,12R,13S-trihydroxy-10E-octadecenoic acid (hereinafter, these are referred to as hydroxy unsaturated fatty acids) is effective as an adjuvant. The following examples confirmed that hydroxy unsaturated fatty acids have the activity of enhancing antibody production against various vaccines and are effective as an adjuvant.

Example 6

Enhancing Effect on Antibody Production by Oral Administration of the Adjuvants in the Secondary Immunization With Intranasally Inoculated Influenza HA Vaccine Purified influenza virus (A/PR/8/34) was defatted by ether treatment to prepare HA vaccine (protein concentration, 50 μg/mL) Aqueous solutions of 9S,12S,13S-trihydroxy-10E-octadecenoic acid, 9S,12R,13S-trihydroxy-10E-octadecenoic acid, or 9R,12R,13S-trihydroxy-10E-octadecenoic acid, synthesized by the method described in Examples 3 to 5 were prepared to give sample solutions. Each hydroxy unsaturated fatty acid solution was given to BALB/c mice (7-week old female) at a dose of 50 ag/kg weight of mouse by forced intragastric administration through an oral probe. On the day of oral administration, the mice were anesthetized with sodium amobarbital and 10 μL (1 ag/mouse) of the vaccine was dropped into both left and right nasal cavities with a micro-pipette. After three weeks, each hydroxyl unsaturated fatty acid solution was given again to mice at a dose of 50 ag/kg by forced intragastric administration, and secondary immunization was performed by dropping 10 μL of a vaccine with a micro-pipette into both left and right nasal cavities on the day of oral administration. One week after the secondary immunization, blood was collected from the heart of the mice to prepare sera. In addition, nasal irrigation liquids were prepared by perfusing 2 mL of a phosphate buffered physiological saline (PBS) containing 0.1% bovine serum albumin (BSA) into left and right nasal cavities of the mice. The titers of anti-influenza virus IgA antibody in the sera and nasal irrigation liquids were determined by enzyme-linked immunosorbent assay (ELISA).

Prior to the assay for anti-influenza virus IgA antibody, each well of the 96-well EIA plate (Immulon 4; Dynex Technologies, Inc.) was first coated with 100 μL of anti-mouse IgA monoclonal antibody (mAb) (Pharmingen) (1 μg/mL) diluted with a coating buffer (10 mM sodium carbonate bicarbonate buffer (pH 9.6) containing 10 μg/mL BSA). The plate was allowed to stand at 37° C. for 3 hours, and then the solution in each well was discarded. Each well was coated with 300 μL of a blocking solution (PBS containing 1% skimmed milk) to avoid non-specific binding. After allowed to stand at 37° C. for 1 hour, the plate was washed with PBS-0.05% Tween-20. An aliquot of the test sample diluted with the Superblock blocking buffer solution (Pierce Chemical) was added to each well. After allowed to stand at room temperature overnight, the plate was washed with PBS-Tween-20. A 100 μL aliquot of biotin-labeled HA vaccine (1 μg/mL) diluted with the blocking solution was added to each well. After allowed to stand while being shaken at room temperature for an hour, the plate was washed with PBS-Tween-20. A 100 μL aliquot of streptavidin-β-galactosidase (Life Technologies) diluted with the blocking solution was added to each well. After allowed to stand while being shaken at room temperature for an hour, the plate was washed with PBS-Tween-20. Further, 100 μL of 0.1 mM 4-methylumbelliferyl-β-galactoside (Sigma) dissolved in 10 mM sodium phosphate buffer (pH 7.0)-containing 0.1 M NaCl, 1 mM $MgCl_2$, 0.1% BSA and 0.1% $NaN_3$ was added to each well and then allowed to stand at 37° C. for 2 hours. Finally, 100 μL of 0.1 M glycine-NaOH buffer (pH 10.3) was added to each well and the reaction was monitored in a fluorescence plate reader (FLOW LABORATORIES) (Ex. 355 nm, Em. 460 nm). ELISA for quantificating anti-influenza virus $IgG_1$ antibody was performed according to the same manner as that for quantificating anti-influenza virus IgA antibody except that anti-mouse $IgG_1$ mAb (manufactured by Pharmingen) was used as a capture antibody.

Figure 2:
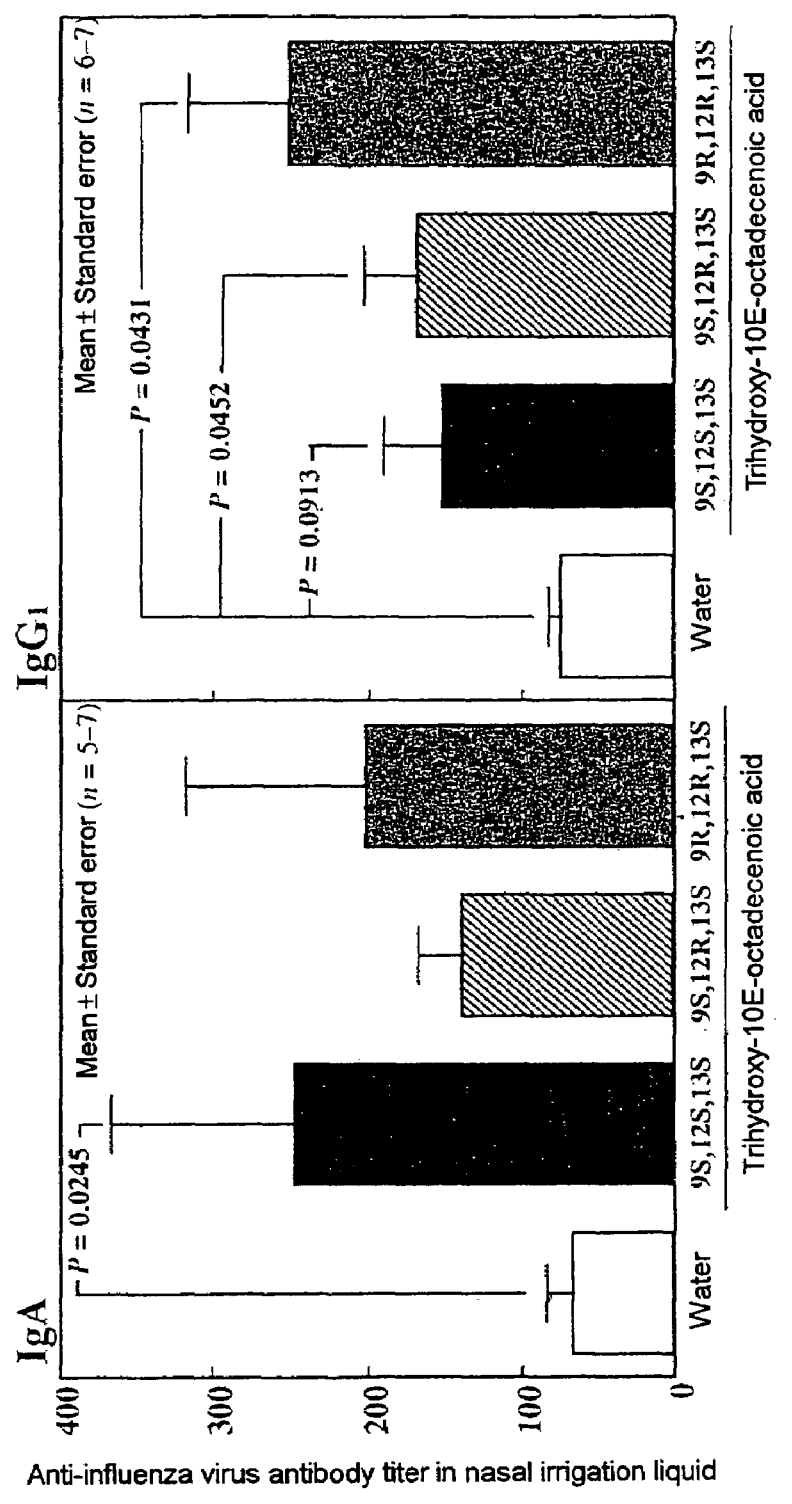

FIG. 2 shows the influence of oral administration of 9S,12S,13S-trihydroxy-10E-octadecenoic acid, 9S,12R,13S-trihydroxy-10E-octadecenoic acid, and 9R,12R,13S-trihydroxy-10E-octadecenoic acid on the titers of anti-influenza virus antibody in nasal irrigation liquids from the mice. When the vaccine was nasally inoculated and an aqueous solvent containing no adjuvant was orally administered, only low levels of the antibodies were detected. However, when 9S,12S,13S-trihydroxy-10E-octadecenoic acid, 9S,12R,13S-trihydroxy-10E-octadecenoic acid, or 9R,12R,13S-trihydroxy-10E-octadecenoic acid is orally administered, the titers of the anti-influenza virus IgA and $IgG_1$ antibodies in the nasal irrigation liquids were strongly enhanced. The results demonstrate that antibody production in nasal cavities induced by the nasally inoculated influenza HA vaccine is enhanced by oral administration of 9S,12S,13S-trihydroxy-10E-octadecenoic acid, 9S,12R,13S-trihydroxy-10E-octadecenoic acid, or 9R,12R,13S-trihydroxy-10E-octadecenoic acid.

Figure 3:
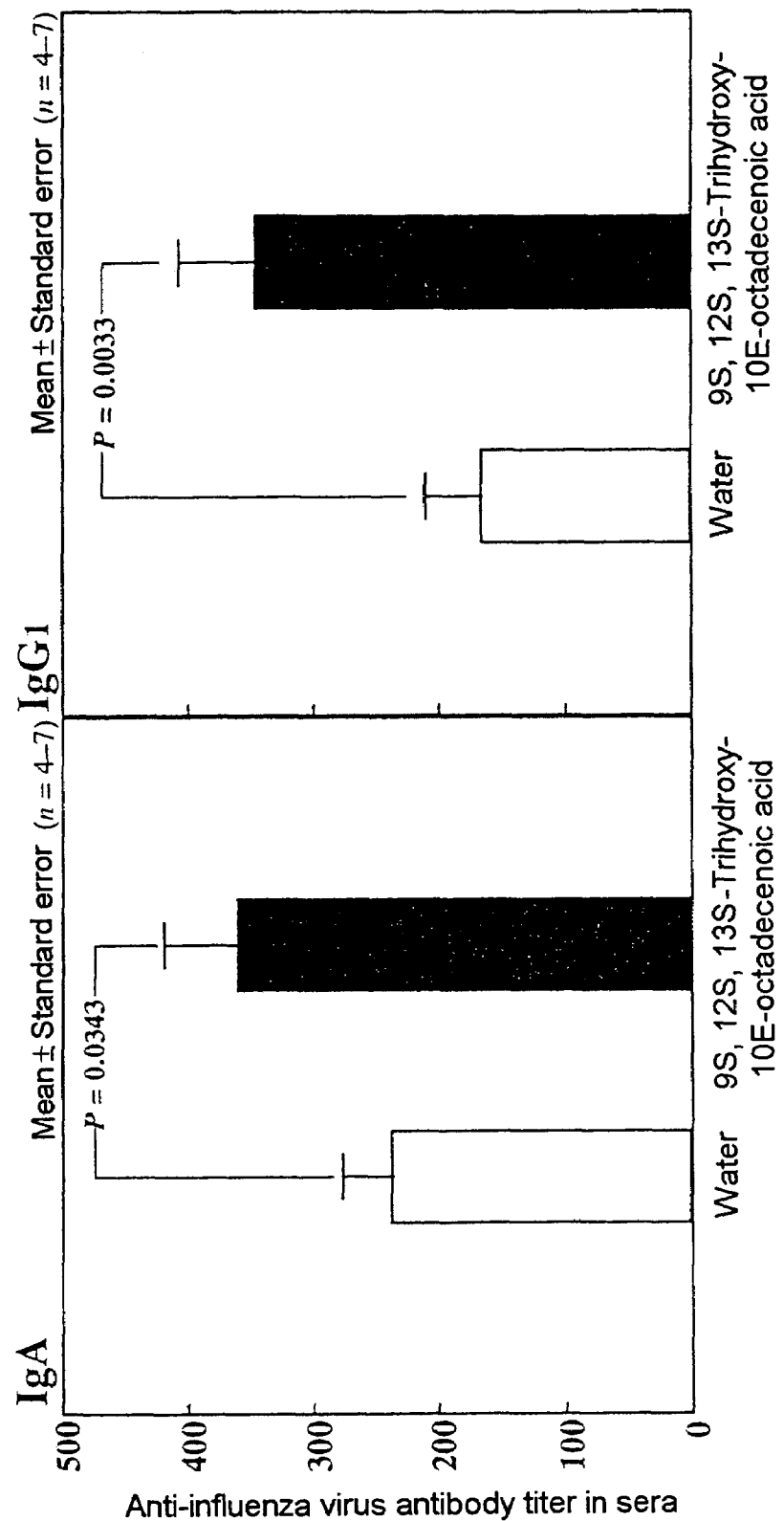
FIG. 3 is a graph showing secondary production of antibodies in sera when an influenza vaccine used as the vaccine of the present invention is intranasally inoculated. The ordinate indicates the antibody titer (ELISA unit) and the abscissa indicates the type of adjuvant used.

FIG. 3 shows the influence of oral administration of 9S,12S,13S-trihydroxy-10E-octadecenoic acid on production of anti-influenza virus IgA and $IgG_1$ antibodies in the sera. When 9S,12S,13S-trihydroxy-10E-octadecenoic acid was orally administered at a dose of 50 μg/kg weight of mouse, the titers of the anti-influenza virus IgA and $IgG_1$ antibodies in the sera were significantly increased compared to the inoculation of the HA vaccine alone. The results demonstrate that production of antibodies in the sera induced by the nasally inoculated influenza HA vaccine is enhanced by oral administration of 9S,12S,13S-trihydroxy-10E-octadecenoic acid.

Next, the presence of antibodies (IgG and IgA) specific to the adjuvant and IgE was detected. A complex of the hydroxy unsaturated fatty acid and BSA that is a carrier protein was prepared. Each well of the 96-well EIA plate was first coated with a 100 μL aliquot of a solution containing the complex (1 μg/mL). Each well of the plate was coated with 300 μL aliquot of a blocking solution (PBS containing 5% skimmed milk) for 1 hour to avoid non-specific reactions. Then, 100 μL samples (nasal irrigation liquid) diluted to various concentrations were added into each well for antigen-antibody reaction, and the reaction was continued for 1 hour. The plate was then washed three times with PBS-0.05% Tween-20, 100 μL of peroxidase-conjugated anti-mouse IgG, IgA or IgE antibody (1:1000) as a secondary antibody was added thereto, and the reaction was continued for one hour. After the plate was washed three times with PBS-Tween-20, 100 μL of a substrate solution (0.1 M citrate buffer (pH 4) containing 0.003% hydrogen peroxide and ABTS of 0.3 mg/mL) was added thereto. The plate was incubated for 15 minutes for color development. The O.D. at 405 nm was measured by a microplate reader. The result showed that no differences in the absorbance of nasal irrigation liquids were recognized between the group of mice to which the hydroxy unsaturated fatty acid had been orally administered and the group of control mice without its administration. According to this result, neither antibodies (IgG, IgA) specific to the adjuvant nor IgE was detected.

As described above, the result that the titers of anti-influenza virus IgA and $IgG_1$ antibodies were elevated by the presence of 9S,12S,13S-trihydroxy-10E-octadecenoic acid, 9S,12R,13S-trihydroxy-10E-octadecenoic acid, and 9R,12R,13S-trihydroxy-10E-octadecenoic acid shows that these compounds orally administered at the time of primary inoculation of the vaccine has the strong effect of inducing the production of antibodies in the respiratory tract at the time of the secondary inoculation of the vaccine. In other words, this means that 9S,12S,13S-trihydroxy-10E-octadecenoic acid, 9S,12R,13S-trihydroxy-10E-octadecenoic acid, and 9R,12R,13S-trihydroxy-10E-octadecenoic acid strongly induce the memory effect on the HA vaccine. As can be predicted from the fact that the hydroxy unsaturated fatty acid used is a low-molecular-weight compound, the result suggests that the compound has only low antigenicity and thus hardly induces side effects.

Example 7

Influenza HA Vaccine-Specific IgE Antibody Production Inhibiting Activity

An influenza HA vaccine and an aqueous solution of 9S,12S,13S-trihydroxy-10E-octadecenoic acid were prepared according to the same manner as in Example 6. A sample solution was given orally to BALB/c mice (7-week old female) at a dose of 50 μg/kg weight of mouse by forced intragastric administration with an oral probe. On the day of oral administration, the mice were anesthetized with sodium amobarbital and 10 μL (1 μg/mouse) of the vaccine was inoculated nasally by dropping into both left and right nasal cavities with a micro-pipette. After breeding the mice for three weeks, a sample solution was orally administered again to the mice, and the vaccine was given by secondary nasal inoculation. After further breeding for 1 week, a bronchoalveolar irrigation liquid was prepared. The bronchoalveolar irrigation liquid was recovered by injecting 2 mL of PBS containing 0.1% BSA into the trachea of the mice after bloodletting and perfusing the lung with the PBS twice. The titer of anti-influenza vaccine IgE antibody in the bronchoalveolar irrigation liquid was measured by ELISA.

Figure 4:
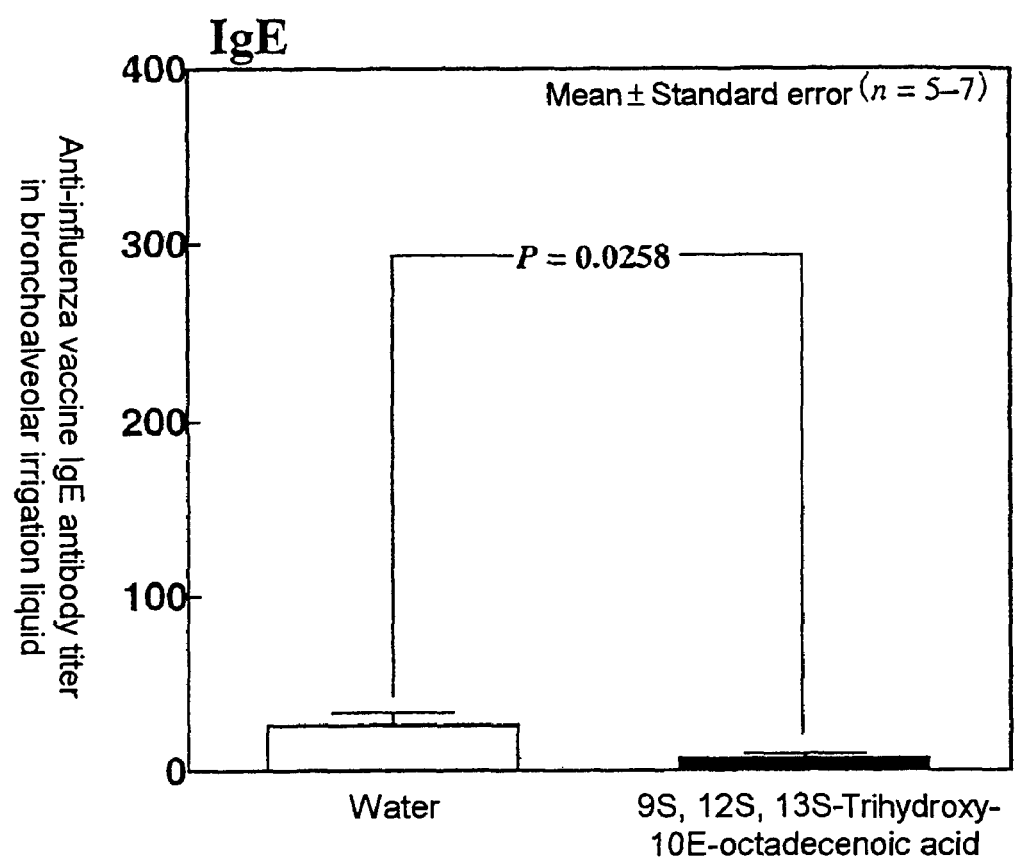
FIG. 4 is a graph showing production of IgE antibody against influenza vaccine in bronchoalveolar irrigation liquids resulting from intranasal inoculation of an influenza vaccine. The ordinate indicates the antibody titer (ELISA unit) and the abscissa indicates the type of adjuvant used.

FIG. 4 shows the influence of oral administration of 9S,12S,13S-trihydroxy-10E-octadecenoic acid on the titer of anti-influenza vaccine IgE antibody in the bronchoalveolar irrigation liquid. When the vaccine was nasally inoculated and an aqueous solvent containing no adjuvant was orally administered, IgE antibody to the influenza vaccine was detected in the bronchoalveolar irrigation liquid, although at an extremely low level. In contrast, when 9S,12S,13S-trihydroxy-10E-octadecenoic acid was orally administered, the titer of the anti-influenza vaccine IgE antibody in the bronchoalveolar irrigation liquid was significantly decreased. The results demonstrate that production of IgE antibody in the lung induced by the nasally inoculated influenza HA vaccine is inhibited by oral administration of 9S,12S,13S-trihydroxy-10E-octadecenoic acid. Since production of IgE antibody to a vaccine is responsible for vaccine side effects such as vaccine allergy and inflammatory response, it is demonstrated that 9S, 12S, 13S-trihydroxy-10E-octadecenoic acid alleviates vaccine side effects.

Example 8

Toxicity of the Hydroxy Unsaturated Fatty Acid

Acute toxicity was studied by administering to mice the hydroxy unsaturated fatty acid (9S,12S,13S-trihydroxy-10E-octadecenoic acid) synthesized in Example 3 and its methyl ester derivative (methyl 9S,12S,13S-trihydroxy-10E-octadecenoate), triacetyl derivative (9S,12S,13S-triacetoxy-10E-octadecenoic acid), and triacetylmethyl ester derivative (methyl 9S,12S,13S-triacetoxy-10E-octadecenoate) prepared from the fatty acid. Structural formulae for 9S,12S,13S-trihydroxy-10E-octadecenoic acid, methyl 9S,12S,13S-trihydroxy-10E-octadecenoate, 9S,12S,13S-triacetoxy-10E-octadecenoic acid, and methyl 9S,12S,13S-triacetoxy-10E-octadecenoate are shown below:

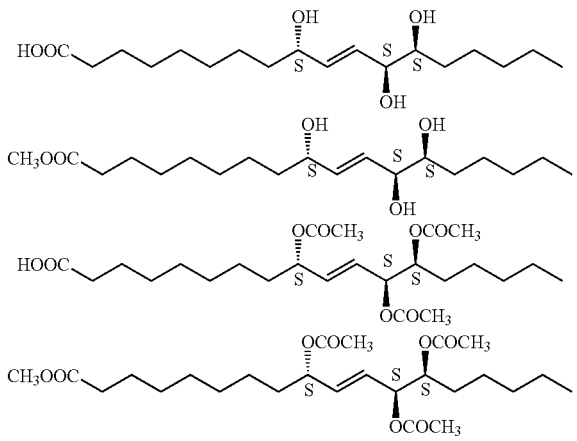

Methyl 9S,12S,13S-trihydroxy-10E-octadecenoate was obtained as follows: 9S,12S,13S-Trihydroxy-10E-octadecenoic acid was dissolved in ether. An excess amount of diazomethane ether solution was added and the mixture was incubated at room temperature for several minutes. The solvent was distilled off from the reaction solution.

9S,12S,13S-Triacetoxy-10E-octadecenoic acid was obtained as follows: 9S,12S,13S-Trihydroxy-10E-octadecenoic acid was refluxed in the presence of sodium acetate in acetic anhydride for about 1 hour, and then the reaction product was subjected to two-phase extraction with chloroform and water to obtain the desired compound from the chloroform layer.

Methyl 9S,12S,13S-trihydroxy-10E-octadecenoate synthesized from 9S,12S,13S-trihydroxy-10E-octadecenoic acid was converted to methyl 9S,12S,13S-triacetoxy-10E-octadecenoate by the same method as for synthesizing 9S,12S,13S-triacetoxy-10E-octadecenoic acid.

These compounds (the purities were 95% or higher) showed no sign of toxicity when intraperitoneally administered at a dose of 30 mg/kg or orally administered at a dose of 100 mg/kg.

Example 9

*Pertussis*-Diphtheria-Tetanus Combined Vaccine (Intranasal)-Hydroxy Unsaturated Fatty Acid (Oral) Preparation Solution of *pertussis*-diphtheria-tetanus combined vaccine was prepared to contain 50 µg of protein nitrogen in 20 µL. 9S,12S,13S-Trihydroxy-10E-octadecenoic acid was dissolved in PBS at a concentration of 10 µg in 0.5 mL and filter sterilized. A preservative (0.005% thimerosal) was added to these solutions. The resulting mixtures were dispensed into containers, which were used as *pertussis*-diphtheria-tetanus combined vaccine (intranasal)-hydroxy unsaturated fatty acid (oral) inoculum preparations. These preparations were stored at a temperature of not more than 10° C. in a cool and dark place.

The *pertussis*-diphtheria-tetanus combined vaccine as prepared above was intranasally inoculated into mice, and 9S,12S,13S-trihydroxy-10E-octadecenoic acid was orally administered before and after the inoculation. After 4 weeks, the same amount of the vaccine was further inoculated, and the antibody production was tested. The test result showed that in the blood from control mice that had been inoculated with only *pertussis*-diphtheria-tetanus combined vaccine, the level of anti-*pertussis* toxin (PT)-IgG antibody was 156 ELISA units; the level of anti-diphtheria toxoid (DT)-IgG antibody was 11 ELISA units; and the level of anti-tetanus toxoid (TT)-IgG antibody was 13 ELISA units, while in the case of the combined use of orally administered 9S,12S,13S-trihydroxy-10E-octadecenoic acid, the level of anti-PT-IgG antibody was 442 ELISA units; the level of anti-DT-IgG antibody was 70 ELISA units; and the level of anti-TT-IgG antibody was 75 ELISA units. Further, while in the nasal irrigation liquid in control mice that had been inoculated only *pertussis*-diphtheria-tetanus combined vaccine, the level of anti-PT-IgA antibody was 6 ELISA units; the level of anti-DT-IgA antibody was 3 ELISA units; and the level of anti-TT-IgA antibody was 4 ELISA units, the level of anti-PT-IgA antibody was 14 ELISA units; the level of anti-DT-IgA antibody was 11 ELISA units; and the level of anti-TT-IgA antibody was 11 ELISA units, in the nasal irrigation liquid in the case of vaccination combined with the administration of 9S,12S,13S-trihydroxy-10E-octadecenoic acid.

Example 10

Measles-Rubella Vaccine (Intranasal)-Hydroxy Unsaturated Fatty Acid (Oral) Preparation A measles-rubella vaccine preparation was prepared to contain virus particles of each vaccine in an amount of 7 µg in 20 µL. 9S,12S,13S-Trihydroxy-10E-octadecenoic acid was dissolved in PBS at a concentration of 2.5 µg in 0.5 mL and filter sterilized. A stabilizer (0.2% porcine gelatin, 0.1% sodium glutamate; 5% lactose) was added to these preparations. The resulting mixtures were dispensed into containers, which were used as measles-rubella combined vaccine (nasal)-hydroxy unsaturated fatty acid (oral) inoculum. These preparations were stored at a temperature of not more than 10° C. in a cool and dark place.

The measles-rubella vaccine as prepared above was nasally inoculated into mice twice at 3-week intervals, and 9S, 12S, 13S-trihydroxy-10E-octadecenoic acid was orally administered only before and after the first inoculation. Then, the antibody production in the blood was evaluated. The test result showed that the ELISA titer of antibody produced was 0.14 for measles and 0.09 for rubella when the vaccine alone had been inoculated, while the titer was 0.30 for measles and 0.29 for rubella in the case of the combined use of 9S, 12S, 13S-trihydroxy-10E-octadecenoic acid with the vaccine.

Example 11

Preparation of Rotavirus Vaccine-Hydroxy Unsaturated Fatty Acid Ester Preparation (Oral Preparation, Nasal Drop)

A rotavirus vaccine preparation was prepared to contain virus particles in an amount of 3.3 μg in 20 μL. The methyl ester derivative (methyl 9S, 12S, 13S-trihydroxy-10E-octadecenoate) as used in Example 8 was dissolved in PBS and prepared at a concentration of 10 μg in 0.5 mL. The resulting preparation was filter sterilized and dispensed into containers, which were used as rotavirus vaccine-hydroxy unsaturated fatty acid ester oral preparations or nasal drops. These preparations were stored at a temperature of not more than 10° C. in a cool and dark place.

The rotavirus vaccine as prepared above was nasally inoculated into mice twice at 3-week intervals, and the methyl ester derivative was orally administered only before and after the first inoculation. Then, the antibody production in the blood was evaluated. The test result showed that the ELISA titer of antibody produced was 0.089 in the inoculation of nasal vaccine drop when the vaccine alone was inoculated, while the titer was 0.38 in the case of the combined use of the methyl ester derivative with the vaccine. Furthermore, the titer was 0.018 in the mice of the control group without adjuvant inoculation when the vaccine had been inoculated orally, while the titer was 0.27 in the group to which the vaccine together with the methyl ester derivative had been inoculated.

Example 12

Preparation of Mycoplasma Vaccine-Hydroxy Unsaturated Fatty Acid Preparation (Nasal Drop, Oral Preparation)

A mycoplasma vaccine was prepared to contain mycoplasma bacteria in an amount of $2.0 \times 10^{10}$ CFU (colony forming unit) in 20 μL. 9S,12S,13S-Trihydroxy-10E-octadecenoic acid was dissolved in PBS at a concentration of 10 μg in 0.5 mL and filter sterilized. These were dispensed into containers, which were used as mycoplasma vaccine-hydroxy unsaturated fatty acids preparation nasal drops or oral preparations. These preparations were stored at a temperature of not more than 10° C. in a cool and dark place.

The mycoplasma vaccine as prepared above was intranasally inoculated into mice three times at 2-week intervals, and then 9S, 12S, 13S-trihydroxy-10E-octadecenoic acid was orally administered only before and after the first inoculation. Then, the lesions associated with Mycoplasma infection were observed. The test result showed that the lesions were recognized in all of 10 control mice to which the vaccine alone had been inoculated, while the lesions were found in only 3 of 10 mice to which 9S, 12S, 13S-trihydroxy-10E-octadecenoic acid had been given together with the vaccine. While the average number of lesions was 302 in the case of the vaccine alone, the number was 178 in the case of the combined use of 9S,12S,13S-trihydroxy-10E-octadecenoic acid with the vaccine.

INDUSTRIAL APPLICABILITY

The Examples shown above clearly indicate the following effect of the present invention.

1. Oral administration of the inventive adjuvant comprising a hydroxy unsaturated fatty acid, in particular 9S,12S,13S-trihydroxy-10E-octadecenoic acid, 9S,12R,13S-trihydroxy-10E-octadecenoic acid, and 9R,12R,13S-trihydroxy-10E-octadecenoic acid, can enhance the production of antibody against the intranasally inoculated influenza HA vaccine and other vaccines.

2. When the inventive adjuvant is orally administered, and a vaccine antigen is inoculated through the intranasal route, not only the antibody production in the blood but also local antibody production (in the nasal cavity) is enhanced. In other words, the inventive adjuvant can reduce the inoculum dose of vaccine antigen, which leads to reduction of the side effects.

3. Since both toxicity and antigenicity of the hydroxy unsaturated fatty acid are sufficiently low, vaccine preparations to be used in combination with the adjuvant of the present invention are highly safe.

As discussed above, vaccine preparations containing as a constituent the adjuvant in accordance with the present invention would be effective drugs that prevent or treat virus and bacterial infections by vaccination.

The invention claimed is:

1. An adjuvant consisting of (i) 9,12,13-trihydroxy-10E-octadecenoic acid or a derivative thereof represented by any one of the formulae (I) or (III);

(I)

$$R_1-\underset{\underset{O}{\|}}{C}\diagup\!\!\!\!\!\diagdown\diagup\!\!\!\!\!\diagdown\diagup\!\!\!\!\!\diagdown\underset{S}{\overset{OR_2}{\vdots}}\diagup\!\!\!\!\!\diagdown\underset{S}{\overset{}{\diagdown}}\!\!\underset{\underset{OR_3}{|}}{\overset{S}{|}}\!\!\diagdown\underset{S}{\overset{OR_4}{|}}\diagup\!\!\!\!\!\diagdown\diagup\!\!\!\!\!\diagdown$$

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group; or (III)

$$R_1-\underset{\underset{O}{\|}}{C}\diagup\!\!\!\!\!\diagdown\diagup\!\!\!\!\!\diagdown\diagup\!\!\!\!\!\diagdown\underset{R}{\overset{OR_2}{|}}\diagup\!\!\!\!\!\diagdown\underset{\underset{OR_3}{\vdots}}{\overset{R}{\underset{S}{|}}}\diagdown\underset{S}{\overset{OR_4}{|}}\diagup\!\!\!\!\!\diagdown\diagup\!\!\!\!\!\diagdown$$

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group, and (ii) a pharmaceutically acceptable carrier.

2. A vaccine preparation consisting of an antigen constituent and the adjuvant of claim 1.

3. The vaccine preparation of claim 2, wherein the adjuvant in the vaccine preparation is orally or transdermally administered independently of an antigen constituent.

4. The vaccine preparation of claim 2, wherein the antigen constituent in the vaccine preparation is inoculated intranasally, subcutaneously, orally, transdermally, intramuscularly, or through mucosa by the other route.

5. The vaccine preparation of claim 2, wherein the antigen constituent is one or more antigens from pathogenic microorganisms selected from the group consisting of influenza virus, rotavirus, measles virus, rubella virus, mumps virus, AIDS virus, *Bordetella pertussis*, diphtheria bacillus, *Helicobacter pylori*, enterohaemorrhagic *Escherichia coli* (EHEC)), *Chlamydia, Mycoplasma*, Malaria *Plasmodium*, coccidium and schistosome.

6. A method for administering the vaccine preparation of claim 2, wherein the method comprises orally or transdermally administering the adjuvant in the vaccine preparation independently of the antigen constituent, wherein the adjuvant is administered concurrently with the antigen constituent.

7. A method for administering the vaccine preparation of claim 2, wherein the antigen constituent is inoculated intranasally, subcutaneously, orally, transdermally, intramuscularly, or through mucosa by the other route, wherein the adjuvant is administered concurrently with the antigen constituent.

8. An adjuvant consisting of (i) 9,12,13-trihydroxy-10E-octadecenoic acid or a derivative thereof represented by any one of the formulae (I) or (III);

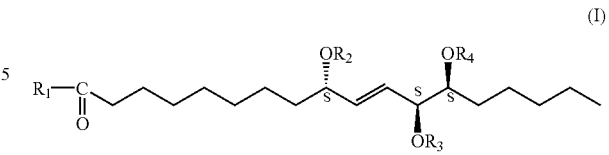

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group; or

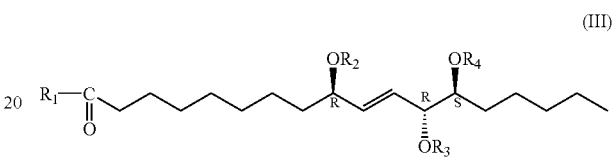

wherein $R_1$ is a hydroxyl group, or an oxygen, sulfur, or nitrogen atom substituted with one or two alkyl or aryl groups; and $R_2$, $R_3$, and $R_4$ may be identical or different and each represents hydrogen, an alkyl group, or an acyl group, and (ii) a pharmaceutically acceptable carrier, wherein contaminants unnecessary for vaccination are not included.

9. The vaccine preparation of claim 2, wherein contaminants unnecessary for vaccination are not included.

* * * * *

UNITED STATES PATENT AND TRADEMARK OFFICE
CERTIFICATE OF CORRECTION

| | | |
|---|---|---|
| PATENT NO. | : 7,560,484 B2 | Page 1 of 1 |
| APPLICATION NO. | : 10/363484 | |
| DATED | : July 14, 2009 | |
| INVENTOR(S) | : Yamada et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1006 days.

Signed and Sealed this
Fifteenth Day of March, 2011

David J. Kappos
*Director of the United States Patent and Trademark Office*